United States Patent
Brugarolas et al.

(10) Patent No.: US 10,442,767 B2
(45) Date of Patent: *Oct. 15, 2019

(54) USE OF FLUORINATED DERIVATIVES OF 4-AMINOPYRIDINE IN THERAPEUTICS AND MEDICAL IMAGING

(71) Applicant: The University of Chicago, Chicago, IL (US)

(72) Inventors: Pedro Brugarolas, Chicago, IL (US); Brian Popko, Chicago, IL (US); Daniel Appelbaum, Chicago, IL (US); Chin-Tu Chen, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/452,179

(22) Filed: Mar. 7, 2017

(65) Prior Publication Data
US 2017/0174629 A1    Jun. 22, 2017

Related U.S. Application Data

(63) Continuation of application No. 14/329,597, filed on Jul. 11, 2014, now Pat. No. 9,617,215, which is a continuation-in-part of application No. 13/897,035, filed on May 17, 2013, now abandoned, which is a continuation-in-part of application No. PCT/US2013/041638, filed on May 17, 2013.

(60) Provisional application No. 61/648,214, filed on May 17, 2012, provisional application No. 61/845,878, filed on Jul. 12, 2013.

(51) Int. Cl.
| | |
|---|---|
| A61K 51/00 | (2006.01) |
| A61M 36/14 | (2006.01) |
| C07D 213/73 | (2006.01) |
| A61K 51/04 | (2006.01) |
| C07D 213/75 | (2006.01) |
| C07B 59/00 | (2006.01) |

(52) U.S. Cl.
CPC ........ *C07D 213/73* (2013.01); *A61K 51/0455* (2013.01); *C07B 59/002* (2013.01); *C07D 213/75* (2013.01)

(58) Field of Classification Search
CPC ............... C07D 213/73; C07D 213/75; A61K 51/0455; C07B 59/002
USPC ........................................................ 424/1.89
See application file for complete search history.

(56) References Cited

U.S. PATENT DOCUMENTS

| | | | |
|---|---|---|---|
| 9,617,215 B2* | 4/2017 | Brugarolas | C07D 213/75 |
| 2004/0171587 A1 | 9/2004 | Borgens et al. | 514/89 |
| 2006/0142179 A1 | 6/2006 | Miller | 514/1.2 |
| 2010/0056584 A1* | 3/2010 | Sorensen | C07D 213/74 514/352 |
| 2010/0087437 A1 | 4/2010 | John | 514/252.12 |
| 2010/0221180 A1 | 9/2010 | Wang et al. | 424/1.77 |
| 2011/0172203 A1 | 7/2011 | Ashwell | 514/210.21 |
| 2011/0224266 A1 | 9/2011 | Miller | 514/352 |

FOREIGN PATENT DOCUMENTS

| | | |
|---|---|---|
| CN | 101863829 | 10/2010 |
| WO | WO 02/072025 | 9/2002 |
| WO | WO 2004/052291 | 6/2004 |
| WO | WO 2007/141529 | 12/2007 |
| WO | WO 2008/074383 | 6/2008 |
| WO | WO 2011/029082 | 3/2011 |

OTHER PUBLICATIONS

"Experimental allergic encephalomyelitis, a useful model for multiple sclerosis. A satellite conference of the International Society of Neurochemists. Seattle, Washington, Jul. 16-19, 1983." *Prog. Clin. Biol. Res.*, 146:1-554. 1984.
Acorda Therapeutics, I. vol. Application No. 02250 (http://www.accessdata.fda.gov/drugsatfda_docs/nda/2010/022250s000TOC.cfm, 2010).
Ametamey et al., *Chem. Rev.*, 108:1501-1516, 2008.
Armstrong and Loboda, *Biophys. J.*, 81:895-904, 2001.
Arroyo et al., *J. Comp. Neural.*, 479:424-434, 2004.
Bak et al., *Acta Chem Scand*. 1958; 12:995-998.
Barnette CRC *Crit. Rev. Biochem*. 1984; 201-235.
Behi et al., *Immunology Lett.*, 96:11-26, 2005.
Bennett, et al., Chem & Industry. 17:1-5, 2010.
Berger, et al., *Arzneimittelforschung*. 39:762, 1989.
Blight, A. R. *Brain Res Bull* 1989, 22, 47-52.
Bohm et al., *ChemBioChem*. 2004; 5: 637-643.
Bowe, C. M., Kocsis, J. D. & Waxman, S. G. Differences between mammalian ventral and dorsal spinal roots in response to blockade of potassium channels during maturation. *Proc R Soc Land B Biol Sci* 224, 355-366 (1985).
Caballero, et al., J Mol Model. DOI: 10/1007/s00894-007-0184-9, 2007.
Cai, et al., *Euro J Org Chem*. 2853, 2008.
Calabresi, P. *Multiple sclerosis and demyelinating conditions of the central nervous system*. 23rd edn, (Saunders Elsevier, 2007).
Choquet, D. & Korn, H. Mechanism of 4-aminopyridine action on voltage-gated potassium channels in lymphocytes. *The Journal of general physiology* 99, 217-240 (1992).
Chun, et al., *Chem Commun (Camb)*. 48:9921, 2012.
Chun, et al., *J Org Chem*. 77(4):1931-8, 2012.

(Continued)

Primary Examiner — Michael G. Hartley
Assistant Examiner — Sean R Donohue
(74) Attorney, Agent, or Firm — Norton Rose Fulbright US LLP

(57) ABSTRACT

The present disclosure provides novel compounds, including compounds that bind to potassium channels, methods for their manufacture, and methods for their use, including their use to diagnose and/or assess traumatic brain injury and use to treat demyelinating diseases, and/or in vivo imaging of the central nervous system, and to diagnose and/or assess the progression of MS or other diseases.

17 Claims, 12 Drawing Sheets

(56) References Cited

OTHER PUBLICATIONS

Coman et al., *Brain*, 129:3186-3195, 2006.
Devaux, J., Gola, M., Jacquet, G. & Crest, M. Effects of K+ channel blockers on developing rat myelinated CNS axons: identification of four types of K+ channels. *Journal of neurophysiology* 87, 1376-1385 (2002).
Dingemanse, E. & Wibaut, J. P. Zur Pharmakologie von einigen Pyridylpyrrolen and einigen Abkömmlingen des α-Aminopyridins. *Naunyn-Schmiedebergs Archie fur experimentelle Pathologie and Pharmakologie* 132, 365-381, doi:10.1007/bf01859845 (1928).
Dolle, et al., *Curr Pharma Des.* 11:3221, 2005.
Eng, D. L., Gordon, T. R., Kocsis, J. D. & Waxman, S. G. Development of 4-AP and TEA sensitivities in mammalian myelinated nerve fibers. *Journal of neurophysiology* 60, 2168-2179 (1988).
Fehlings, M. G. & Nashmi, R. Changes in pharmacological sensitivity of the spinal cord to potassium channel blockers following acute spinal cord injury. *Brain research* 736, 135-145 (1996).
Ferrieri et al., *Handbook Radiopharm.: Radiochem. Appl.* 2003; 229-282.
Flygt, J et al., *Eur J Neurosci* 2013, 38, 2153-65.
Gao et al., *Neurochem. Res.*, 24:1181-1188, 1999.
Gobel, K. et al. 4-Aminopyridine ameliorates mobility but not disease course in an animal model of multiple sclerosis. *Experimental neurology* 248C, 62-71, doi:10.1016/j.expneurol.2013.05.016 (2013).
Goodman et al., *Lancet.*, 373:732-738, 2009.
Gruner, J. A. and Yee, A. K., *Brain Res* 1999, 816, 446-56.
Gutman, et al., *Pharmacal Rev.* 57:473, 2005.
Hayes, K. C, et al., *Paraplegia* 1993, 31, 216-24.
http://goo.gl/fqcZo; accessed Jan. 14, 2014.
Kiferle et al., "Positron emission tomography imaging in multiple sclerosis—current status and future applications," *European Journal of Neurology* 18(2):226-231, 2011.
Kirsch and Narahashi, *Biophys. J.*, 22:507-512, 1978.
Kocsis, J. D. Aminopyridine-sensitivity of spinal cord white matter studied in vitro. *Experimental brain research. Experimentelle Hirnforschung. Experimentation cerebrale* 57, 620-624 (1985).
Lasne et al., *Top. Curr. Chem.* 2002; 201-258.
Lee and Chi, *J. Organic Chem.*, 64:8576-8581, 1999.
Lee et al., *Bull. Korean Chem. Soc.*, 25(8):1225-1230, 2004.
Lee et al., *Science*, 334:639-642, 2011.
Lee, et al., *J Org Chem.* 64:8576, 1999.
Leung et al., *Exp. Neural.*, 227:232-235, 2011.
Lin et al., *J. Neurosci.*, 24:10074-10083, 2004.
Lundh et al., *J. Neural. Neurosurg. Psychiatry*, 40(11):1109-1112, 1977.
Maddison and Newsom-Davis, *Cochrane Database Syst. Rev.*, CD003279, 2003.
Manteau et al., *Eur. J. Org. Chem.* 2010, 6043-6066.
Martin and McFarland, *Crit. Rev. Clin. Lab. Sci.*, 32:121-182, 1995.
Matsushima and Morell, *Brain Pathol.*, 11:107-116, 2001.
McBride, et al., *Euro J Pharm Sci.* 27:237-42, 2006.
McCormack, et al., *Neuron.* 12:301, 1994.
Mobinikhaledi and Foroughifar, *Phosphorus, Sulfur and Silicon*, 181:405-412, 2006.
Mochizuki, et al., *Bioorg Med Chem.* 19:1623, 2011.
Morey, R. A.; et al,. *Hum Brain Mapp.* 34(11): 1-21, 2013.
Muller, K., Faeh, C. & Diederich, F. Fluorine in pharmaceuticals: looking beyond intuition. *Science* 317, 1881-1886, doi:10.1126/science.1131943 (2007).
Murray and Newsom-Davis, *Neurology*, 31:265-271, 1981.
Olah et al., *Acta Chim. Acad. Scien. Hung.* 1955; 443-449.
Olek, M. J. (ed Francisco Gonzalez-Scarano (Ed)) (Waltham, MA, UpToDate, 2011).
Oriuchi et al., *Cancer Sci.*, 97:1291-1297, 2006.
Owen et al., *Mult. Scler.*, 17:262-272, 2011.
Park, B. K., Kitteringham, N. R. & O'Neill, P. M. Metabolism of fluorine-containing drugs. *Annu Rev Pharmacol Toxicol* 41, 443-470, doi:10.1146/annurev.pharmtox.41.1.443 (2001).
PubChem (CID 10796739) 4-aminopyridine-3-methanol. URL: http://pubchem.ncbi.nlm.nih.gov/summary/summary.cgi?cid=10796739.
PubChem (CID 23583877) 4-aminopyridin-3-ylboronic acid. URL: http://pubchem.ncbi.nlm.nih.gov/summary/summary.cgi?cid=23583877.
PubChem (CID 45079443) 2-(4-aminopyridin-3-yl)ethanol. URL: http://pubchem.ncbi.nlm.nih.gov/summary/summary cgi?cid=45079443.
Rasband et al., *J. Neurosci.*, 18:36-47, 1998.
Ritchie et al., *Nature*, 294:257-259, 1981.
Roger, et al., *Bioorgan & Med Chem.* 11:5333-43, 2003.
Search Report and Written Opinion in International Application No. PCT/US2013/41638 dated Nov. 15, 2013.
Sharp, D. J. and Ham, T. E. *Curr Opin Neurol* 2011, 24, 558-63.
Sherratt, R. M., Bostock, H. & Sears, T. A. Effects of 4-aminopyridine on normal and demyelinated mammalian nerve fibres. *Nature* 283, 570-572 (1980).
Smith et al., *Eur. J. Medicinal Chem.*, 40:908-917, 2005.
Soni and Kam, *Anaesth Intensive Care*, 10(2):120-126, 1982.
Spivey et al., *J. Org. Chem.*, 64(26):9437, 1999.
Stankoff, B. et al. Imaging central nervous system myelin by positron emission tomography in multiple sclerosis using [methyl-(1)(1)C]-2-(4'-methylaminophenyl)-6-hydroxybenzothiazole. *Annals of neurology* 69, 673-680, doi:10.1002/ana.22320 (2011).
Starace and Bezanilla, *Nature*, 427:548-552, 2004.
Stefani, E. & Bezanilla, F. Cut-open oocyte voltage-clamp technique. *Methods Enzymol* 293, 300-318 (1998).
Stidworthy et al., *Brain*, 127:1928-1941, 2004.
Stys et al., *Brain Res.*, 546(1):18-32, 1991.
Sun et al., *J. Neuropharmacol.* 2010; 193: 469-478.
Sun, J. *Chem. Inf. Comput. Sci.*, 44(2):748-757, 2004.
Takano, A. et al. In vivo TSPO imaging in patients with multiple sclerosis: a brain PET study with [18F]FEDAA1106. *EJNMMI research* 3, 30, doi:10.1186/2191-219X-3-30 (2013).
Traka et al., *Brain*, 133:3017-3029, 2010.
Valk, P. E. *Positron emission tomography : basic science and clinical practice.* (Springer, 2003).
Wang et al., *Neuron.*, 15:1337-1347, 1995.
Waxman and Ritchie, *Ann. Neurol.*, 33:121-136, 1993.
Wu, C. et al. A novel PET marker for in vivo quantification of myelination. *Bioorganic & medicinal chemistry* 18, 8592-8599, doi:10.1016/j.bmc.2010.10.018 (2010).
Wu, C. et al. Longitudinal PET imaging for monitoring myelin repair in the spinal cord. *Annals of neurology*, doi:10.1002/ana.23965 (2013).
Wulff et al., *Nat. Rev. Drug Discov.*, 8:982-1001, 2009.
Zamvil and Steinman, *Annu. Rev. Immunol.*, 8579-8621, 1990.
Zhang et al., *Curr. Top. Med. Chem.* 2007; 7:1817-1828.
Zhou et al., *J. Med. Chem.*, 52:2443-2453, 2009.

\* cited by examiner

USE OF FLUORINATED DERIVATIVES OF 4-AMINOPYRIDINE IN THERAPEUTICS AND MEDICAL IMAGING

CROSS-REFERENCE TO RELATED APPLICATIONS

This application is a continuation of U.S. patent application Ser. No. 14/329,597 filed Jul. 11, 2014, which is a continuation-in-part of U.S. patent application Ser. No. 13/897,035 filed May 17, 2013 and PCT Application PCT/US2013/041638 filed May 17, 2013, both of which claim priority to U.S. Provisional Patent Application Ser. No. 61/648,214 filed May 17, 2012. U.S. patent application Ser. No. 14/329,597 also claims the benefit of priority to U.S. Provisional Patent Application Ser. No. 61/845,878 filed Jul. 12, 2013. The entire contents of each of the above-referenced disclosures are specifically incorporated herein by reference without disclaimer.

BACKGROUND OF THE INVENTION

I. Field of the Invention

The present invention relates generally to the fields of biology, chemistry and medicine. More particularly, it concerns derivatives of potassium channel inhibitors, including derivatives of 4-aminopyridine, and methods of making and using thereof, including for the treatment and medical imaging of neurodegenerative conditions.

II. Description of Related Art

With nearly 400,000 people affected in the U.S. and 2.5 million worldwide, Multiple Sclerosis (MS) is the most common neurodegenerative condition in young adults (Calabresi, 2007). The progressive demyelination of neurons in the brain leads to diverse neurological symptoms. Myelin is the multilayered membrane that surrounds most axons of the central and peripheral nervous systems and is essential for the propagation of rapid nerve impulses. In people with MS, the myelin sheath that normal covers the axons is lost and this leads to aberrant leakage of potassium ions from the axon and improper impulse conduction.

One approach to treat MS or to mitigate the symptoms associated with MS is to block potassium channels to reduce the leakage of potassium ions, thus enhancing impulse conduction. In January 2010, the FDA approved 4-aminopyridine (4-AP), as a therapy for MS (Ampyra, Acorda Therapeutics, Inc., 2010). 4-AP is a relatively selective blocker of $K_v1$ family of $K^+$ channels (Wulff et al., 2009). By blocking $K^+$ channels, impulse conduction along the axon is partially restored and symptoms ameliorate.

To develop new neuroprotective therapies for MS or other neurodegenerative diseases, it is essential to have proper tools to diagnose and assess disease progression.

According to CDC around 1.74 million people sustain a traumatic brain injury in the U.S. each year. Most of these injuries are mild (75%) and certain populations are at a higher risk: men aged 0-4, 15-19 and over 60 as well as military personnel and people engaged in contact sports. Recent studies have shown that even mild TBIs can have serious consequences later in life. TBI has been linked to depression, anxiety, substance abuse and suicide. All these reasons make screening for TBI particularly important.

Currently, the diagnosis of TBI is based on clinical evaluation aided by Computed Tomography (CT) or Magnetic Resonance Diffusion Tensor Imaging (MR-DTI). CT scans are very useful for detecting mass lesions and fractures but do not allow visualization of mild TBIs. More recently, MR-DTI has emerged as a sensitive method to evaluate white matter integrity in TBI but it too can be difficult to interpret.

During TBI, compression or stretching of the brain often causes damage to axons and/or the myelin sheath. Oligodendrocytes, the cells responsible for producing and maintaining myelin, have also been shown to be sensitive to TBI (Flygt et al., 2013; Sharp and Ham, 2011; Morey et al., 2012). Oligodendrocyte injury results in axonal demyelination. In addition to facilitating raping nerve conduaction velocities, myelin provides axonal protection, such that demyelinated axons are prone to degeneration. Therefore, TBI-induced damage to myelin and/or oligodendrocytes likely contributes to the acute and long-term clinical manifestations of TBI.

Axonal proteins are compartmentalized in myelinated axons, with the voltage-gated sodium channels concentrated at the unmyelinated node of Ranvier and the rectifying potassium (K+) channels residing under the myelin sheath (Waxman and Ritchie, 1993). Following demyelination, like that which occurs in multiple sclerosis (MS) and TBI, the K+ channels become exposed and leaky. In 2010, the FDA approved 4-amino-pyridine (4-AP, Ampyra®) as a drug to improve symptoms in people with MS. 4-AP is a K+ channel blocker that binds to the exposed channels on demyelinated axons, which reduces the aberrant efflux of K+ ions and enhances neuronal conduction. Since 4-AP selectively targets K+ channels that have become uncovered as a result of demyelination we propose to test its usefulness as a tracer for demyelinated axons.

Not much is known about the role of axonal K+ channels and the effects of 4-AP in TBI. However, there have been numerous studies looking at the effects of 4-AP after Spinal Cord Injury (SCI; Blight et al., 1989; Blight et al., 1991; Hayes et al., 1993; Fehlings and Nashmi, 1996; Gruner and Yee, 1999). Similarly to TBI, SCI is an injury to the CNS that occurs after a violent impact. Depending on the location and severity of the injury the symptoms can vary from partial loss of movement and sensation (incomplete injury) to complete loss. In cases of incomplete injury, 4-AP has been shown to enhance neuronal conduction through injured areas both in animals and in humans (Blight et al., 1989; Blight et al., 1991; Hayes et al., 1993). In addition, injured spinal cord areas have been shown to have higher pharmacological sensitivity to 4-AP (Fehlings and Nashmi, 1996), which agrees with our hypothesis that K+ channels on demyelinated fibers are more accessible and suggest the potential of using radioactive 4-AP to map injured areas. The similarities between TBI and SCI in etiology and at the histopathological level justify evaluating 4-AP based PET tracers for TBI. In addition, if 4-AP is found to localize to injured areas in TBI it could also be useful for restoring function/ameliorating symptoms in TBI patients. Fluorine-18 is the preferred isotope for PET imaging because its long half-life allows for off-site production and commercialization. In addition, its low positron energy gives higher resolution than for example carbon-11. We have also shown that these fluorinated molecules have very similar properties to 4-AP both in vitro and in vivo indicating that fluorination does not disrupt its properties and therefore these molecules could be used as surrogates of 4-AP.

Thus, there is a pressing need for new, accurate methods to evaluate and diagnose TBI.

SUMMARY OF THE INVENTION

In some embodiments, there are provided compounds that bind to potassium channels, methods for their manufacture, and methods for their use. In a particular embodiment, the compounds may be compounds of formula (I):

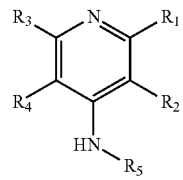

(I)

wherein $R_1$, $R_2$, $R_3$, and $R_4$ are each independently selected from the group consisting of H, $(CH_2)_nX$, $CH_2OCH_2CH_2X$, $NH_2$, $CH_2OH$, $CF_3$, $OCH_3$, $OCH_2F$, $OCHF_2$, $OCF_3$ and $R_5$ is selected from the group consisting of H, $(CH_2)_mX$, OH, $COOCF_3$, $COOC(CH_3)_3$, and $COO(CH_2)_mX$; wherein n=0, 1, 2, 3, 4, or 5 and m=2, 3, 4, or 5; wherein X represents a fluorine atom or an isotope thereof; as well as pharmaceutically acceptable salts, tautomers, or deuterated versions thereof.

In one aspect, the isotope of fluorine is a radioactive isotope. In a particular aspect, the fluorine isotope is $^{18}F$. In some aspects, any of C, N, O is optionally replaced by an isotope thereof. An isotope of C, N, O may be any known C, N, O isotope. In particular aspects, the isotope is a radioisotope. For example, any of C, N, O may be optionally replaced by the isotope $^{11}C$, $^{13}N$, $^{15}O$, respectively.

In further embodiments, at least one of $R_1$, $R_2$, $R_3$, $R_4$ and $R_5$ is not hydrogen. In still further embodiments, at least one of $R_1$, $R_2$, $R_3$, $R_4$ and $R_5$ contains a fluorine atom or an isotope thereof. In certain aspects, when $R_2$ is $NH_2$, $CH_2OH$, a nonradioactive fluorine, or $CF_3$, at least one of $R_1$, $R_3$, $R_4$, and $R_5$ is not hydrogen. In additional aspects, when $R_4$ is $NH_2$, $CH_2OH$, a nonradioactive fluorine, or $CF_3$, at least one of $R_1$, $R_2$, $R_4$, and $R_5$ is not hydrogen.

In some embodiments, the compounds are not the following compounds:

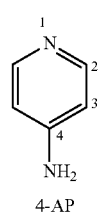

4-AP

A

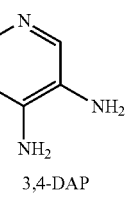

3,4-DAP

B

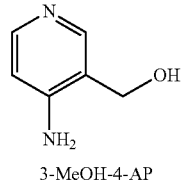

3-MeOH-4-AP

C

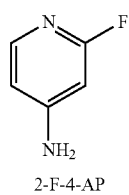

2-F-4-AP

D

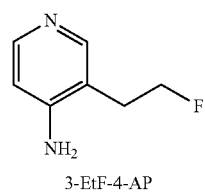

3-EtF-4-AP

G

In some embodiments, the compounds have the following formulas:

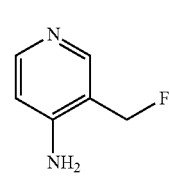

3-MeF-4-AP

E

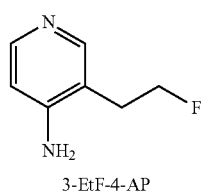

3-EtF-4-AP

F

In certain embodiments, there are provided compounds of formula (II):

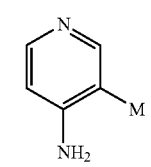

(II)

wherein M is $(CH_2)_nY$ and wherein n=0, 1, or 2, and Y is fluorine or an isotope thereof, as well as pharmaceutical acceptable salts, tautomers, or deuterated versions thereof.

In certain embodiments, M is $CH_2F$, or $(CH_2)_2F$. In further embodiments, M is $^{18}F$, $CH_2^{18}F$, or $(CH_2)_2^{18}F$. In some aspects, any of C, N, O is optionally replaced by an isotope thereof. An isotope of C, N, O may be any known C, N, O isotope. In particular aspects, the isotope is a radioisotope.

For example, any of C, N, O may be optionally replaced by the isotope $^{11}C$, $^{13}N$, $^{15}O$, respectively.

In certain embodiments, there are provided compounds of formula (III):

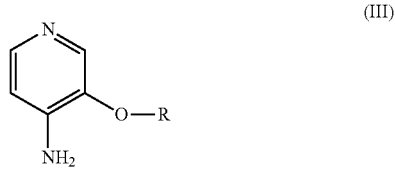

(III)

wherein R is selected from the group consisting of $CH_3$, $CH_2F$, $CHF_2$, and $CF_3$, and wherein C is substituted by $^{11}C$ or at least one of F is substituted by $^{18}F$ in R. For instance, R is $^{11}CH_3$, $CH_2{}^{18}F$, $CHF^{18}F$, $CH(^{18}F)_2$, $C^{18}FF_2$, $C(^{18}F)_2F$, or $C(^{18}F)_3$.

Certain embodiments are directed to the compounds of formula (IV):

(IV)

wherein R is selected from the group consisting of $CF_3$, $CH_2F$, $CH_3CH_2F$, $C(CH_3)_3$, and wherein at least one of F or H in the R group is substituted by $^{18}F$. Non-limiting examples include $CH_2{}^{18}F$, $CHF^{18}F$, $CH(^{18}F)_2$, $C^{18}FF_2$, $C(^{18}F)_2F$, $C(^{18}F)_3$, $CH_3CH_2{}^{18}F$, and $C(CH_3)_2{}^{18}F$.

In some aspects, any of C, N, O in the compounds described herein is optionally replaced by an isotope thereof. An isotope of C, N, O may be any known C, N, O isotope. In particular aspects, the isotope is a radioisotope. For example, any of C, N, O in the compounds of formula (I)-(IV) may be optionally replaced by the isotope $^{11}C$, $^{13}N$, $^{15}O$, respectively.

In some embodiments there are provided pharmaceutical compositions comprising one or more of the above compounds and a pharmaceutically acceptable carrier. In some embodiments, the pharmaceutical compositions further comprise one or more pharmaceutically acceptable excipients. In some embodiments, the composition is formulated for controlled release of any of the compounds disclosed herein.

Certain embodiments are directed to a kit comprising one or more of the above compounds. In further aspects, there are provided a kit comprising one or more of the above compounds comprising a radioisotope.

In some embodiments, there are provided imaging methods comprising administering to a subject in need thereof the imaging agent described herein and detecting the compound comprised in the imaging agent in the subject. In some aspects, the amount of the compound in the subject is quantified. In further aspects, a demyelinated region in an axon in the subject is detected via a detection of the compound in the subject. In still further aspects, the compound administered to the subject may block potassium channels located at the demyelinated region in an axon in the subject.

In certain embodiments, the imaging is effected by a radiodiagnostic method. The radiodiagnostic method may be performed by any instrument capable of detecting radiation by the compounds. Exemplary radiodiagnostic methods include, but not limited to, Positron Emission Tomography (PET), PET-Time-Activity Curve (TAC) or PET-Magnetic Resonance Imaging (MRI). In particular aspect, the radiodiagnostic method is PET.

Certain embodiments are directed to an imaging agent comprising a compound described herein wherein the compound contains an isotope. In some embodiments, the isotopes are isotopes of F, O, N and C. In particular aspects, the isotope is a fluorine isotope. In further embodiments, the isotope is a radioisotope. In still further embodiments, the radioisotope is $^{18}F$, $^{15}O$, $^{13}N$ or $^{11}C$. In particular embodiments, the isotope is $^{18}F$. For example, an imaging agent may comprise a derivative of 4-AP, including, but not limited to, [$^{18}F$]-3-fluoro-4-aminopyridine, [$^{18}F$]-3-fluoro-methyl-4-aminopyridine, and [$^{18}F$]-3-fluoro-ethyl-4-aminopyridine.

In some embodiments, there are provided methods the use of novel compounds as described herein, including for the treatment and/or in vivo imaging of the central nervous system to diagnose and/or assess the progression of MS or other diseases.

In some embodiments, there are provided methods for diagnosing traumatic brain injury (TBI) or evaluating the progression of TBI comprising administering to a subject in need thereof an imaging agent described herein and detecting the compound comprised in the imaging agent in the subject.

In some embodiments, there are provided methods of treating a demyelinating disease or mitigating a symptom of a demyelinating disease comprising administering to a subject in need thereof an effective amount of a compound as defined above.

In further embodiments, there are provided methods of treating TBI or mitigating a symptom of TBI comprising administering to a subject in need thereof an effective amount of a compound as defined above.

It is specifically contemplated that in certain embodiments, methods related to therapy and/or diagnostics involve a subject that is a human patient.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Effective amount" or "therapeutically effective amount" or "pharmaceutically effective amount" means that amount which, when administered to a subject or patient for treating a disease, is sufficient to effect such treatment for the disease. In some embodiments, the subject is administered at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, or 100 mg/kg (or any range derivable therein).

The amount of the compound that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/kilogram (kg) or mg/kg, or any range derivable therein. In some aspects, the pharmaceutically effective amount comprises a dose from about 0.0001 mg/kg/day to about 100 mg/kg/day. In further aspects, the effective amount comprises a dose from about 0.01 mg/kg/day to about 5 mg/kg/day. In still further aspects, the dose is about 0.25 mg/kg/day.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient.

In some embodiments, the compounds described herein are comprised in a pharmaceutical composition. In further embodiments, the compounds described herein and optional one or more additional active agents, can be optionally combined with one or more pharmaceutically acceptable excipients and formulated for administration via epidural, introperitoneal, intramuscular, cutaneous, subcutaneous or intravenous injection. In some aspects, the compounds or the composition is administered by aerosol, infusion, or topical, nasal, oral, anal, ocular, or otic delivery. In further embodiments, the pharmaceutical composition is formulated for controlled release.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., *Verlag Helvetica Chimica Acta*, 2002).

In certain embodiments, the demyelinating disease includes, but is not limited to, multiple sclerosis, spinal cord compression, ischemia, acute disseminated encephalomyelitis, optic neuromyelitis, leukodystrophy, progressive multifocal leukoencephalopathy, metabolic disorders, toxic exposure, congenital demyelinating disease, peripheral neuropathy, encephalomyelitis, central pontine myelolysis, Anti-MAG Disease, Guillain-Barre syndrome, chronic inflammatory demyelinating polyneuropathy, or multifocal motor neuropathy (MMN). In particular embodiments, the demyelinating disease is multiple sclerosis.

In additional embodiments, leukodystrophy includes, but is not limited to, adrenoleukodystrophy, Alexander's Disease, Canavan Disease, Krabbe Disease, Metachromatic Leukodystrophy, Pelizaeus-Merzbacher Disease, vanishing white matter disease, Refsum Disease, Cockayne Syndrome, Van der Knapp Syndrome, or Zellweger Syndrome.

In some embodiments, there are provided methods for diagnosing a demyelinating disease or evaluating the progression of a demyelinating disease comprising administering to a subject in need thereof the imaging agent described herein and detecting the compound comprised in the imaging agent in the subject. In certain aspects, the compound is detected by a radiodiagnostic method, including, but not limited to PET, TAC, or PET-MRI. In particular aspects, the compound is detected by PET.

In some aspects, the subject is a mammal. In particular aspects, the subject is a human. In additional aspects, the subject is a healthy individual. In further aspects, the subject is a verified or putative animal model of myelin-associated neuropathy. For example, in some embodiments, the animal model is DTA model, cuprizone-induced demyelination model, a lysolecithin injection model or experimental autoimmune encephalomyelitis (EAE) model. In still further aspects, the animal model is a mouse mutant with altered nodal environ, including, but not limited to, shiverer, trembler, jimpy, PO null, E-cadherin null, Mag null, Dystrophic laminin α2, Cgt null, Contactin null, Caspr null, Cst null, Caspr2 null, Tag1 null, Dystroglycan, quivering Spectrin βIV, Nrcam null, and Na+ channel β2 null.

In some embodiments, the subject is at risk for traumatic brain injury or a concussion. In some embodiments, the subject has a concussion or has symptoms of a concussion. In some embodiments, the subject is an athlete or participates in athletic activities such as football, hockey, soccer, lacrosse, rugby, field hockey, horseback riding, bull riding, cheerleading, gymnastics, motocross, boxing, wrestling, base jumping, mountaineering, mixed martial arts, parkour, sky diving, free climing, skateboarding, surfing, luge, cliff diving, snowboarding, skiing, pole vault, martial arts, cycling, racing, mountain biking, skating, cricket, basketball, roller derby, softball, baseball, polo, water polo, or other activities.

In some embodiments, there are provided methods for synthesizing the compounds described herein. For example, 3-fluoromethyl-4-aminopyridine or 3-fluoroethyl-4-aminopyridine is produced by a method comprising (a) protecting the amino group of 4-aminopyridine-3-methanol or 4-aminopyridine-3-ethanol with a protection group to form a first intermediate compound, (b) fluorinating the first intermediate compound by using a fluoro-containing reagent to form a second intermediate compound, and (c) removing the protection group from the second intermediate compound to form 3-fluoromethyl-4-aminopyridine or 3-fluoroethyl-4-aminopyridine. In certain aspects, the protection group is Boc (N-tert-butoxycarbonyl). In further aspects, the fluoro-containing reagent is XtalFluor E ((Diethylamino)difluorosulfonium tetrafluoroborate).

In additional aspects, 3-fluoroethyl-4-aminopyridine may be synthesized by a method comprising (a) converting 4-(Boc-amino)pyridine to 4-(Boc-amino)pyridine-3-ethanol, (b) fluorinating 4-(Boc-amino)pyridine-3-ethanol by using Xtal-Fluor, and c) removing Boc to form 3-fluoroethyl-4-aminopyridine.

Methods for producing the fluorine isotope containing compounds describe herein are also contemplated. For example, [$^{18}$]-3-fluoro-4-aminopyridine is produced by a method comprising (a) converting a compound having the structure A (4-(Boc-amino)pyridine) to an intermediate compound with structure B, and (b) fluorinating the intermediate structure B to form [$^{18}$F]-3-fluoro-4-aminopyridine. A [$^{18}$F]-containing reagent is supplied in the fluorination step.

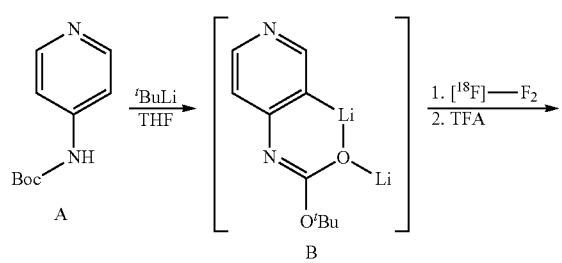

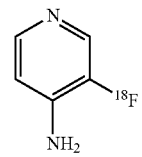

A method for producing [$^{18}$F]-3-fluoromethyl-4-aminopyridine or [$^{18}$F]-3-fluoroethyl-4-aminopyridine is also provided. The method comprises (a) protecting the amino group of 4-aminopyridine-3-methanol or 4-aminopyridine-3-ethanol with a protection group to form a first intermediate compound, (b) fluorinating the first intermediate compound by using a [$^{18}$F]-containing reagent to form a second intermediate compound, and (c) removing the protection group from the second intermediate compound to form [$^{18}$F]-3-fluoromethyl-4-aminopyridine or [$^{18}$F]-3-fluoroethyl-4-aminopyridine. In particular aspects, the protection group is Boc (N-tert-butoxycarbonyl).

In additional aspects, [$^{18}$F]-3-fluoroethyl-4-aminopyridine may be synthesized by a method comprising (a) converting 4-(Boc-amino)pyridine to 4-(Boc-amino)pyridine-3-ethanol, (b) fluorinating 4-(Boc-amino)pyridine-3-ethanol by using a [$^{18}$F]-containing reagent, and (c) removing Boc to form [$^{18}$F]-3-fluoroethyl-4-aminopyridine.

In certain embodiments, the [$^{18}$F]-containing reagent includes, but is not limited to, [$^{18}$F]-Kryptofix, [$^{18}$F]—F2, [$^{18}$F]—AcOF, [$^{18}$F]F-TEDA, [$^{18}$F]-Benzo[h]quinolinyl (tetrapyrazolylborate) Pd(IV) fluoride trifluoromethanesulfonate, [$^{18}$F]-2-fluoroethyl bromide, and [$^{18}$F]-fluoromethyl-bromide. In particular aspects, the [$^{18}$F] containing reagent is [$^{18}$F] Kryptofix.

In some embodiments, an alternative method for producing [$^{18}$F]3-fluoro-4-aminopyridine is provided, comprising the steps of (a) using Koser's reagent to iodonate 4-(Boc-amino)pyridin-3-ylboronic acid to form a first intermediate compound, (b) fluorinating the intermediate compound by using a [$^{18}$F]fluor-containing reagent, and (c) using HCl to remove the protecting group to yield [$^{18}$F]3-fluoro-4-aminopyridine.

The methods for producing the compounds described herein are not limited to the exemplary methods described herein. The compounds may be synthesized by any suitable method known in the art and it will be obvious to those skilled in the art that various adaptations, changes, modifications, substitutions, deletions or additions of procedures may be made without departing from the spirit and scope of the invention.

In certain methods and compositions, embodiments concern the use of a compound for research purposes involving a potassium channel blocker. The compound may be used for its potassium channel blocking activity. Therefore, in some embodiments, methods involve exposing, contacting, or adding a compound discussed herein to a channel or a polypeptide involved in channel activity and determining calcium channel activity. In some embodiments, the compound is a control. In other embodiments, the compound is used to screen other compounds for an activity that affects channel activity (such as by inhibiting or enhancing that activity).

Because of the biological activity of the compounds disclosed herein, in additional embodiments, there are methods and compositions for use of these compounds as an avicide. In some embodiments, a compound discussed herein is formulated as grain bait, a powder concentrate or a liquid for exposure to or ingestion by birds. The LD50 for birds is generally in the range of about 100 parts per million (ppm) to 1000 parts per million, and dosages are formulated to provide at least that much to birds. Embodiments also include methods of using an avicide comprising providing to an avian an effective amount of a composition comprising a compound discussed herein, including but not limited to those having Formula I or Formula II. In certain embodiments, providing the compound comprises distributing the composition to places that birds can access, including but not limited to distributing it in grass, trees, bushes, on leaves, in bird feeders or in bird baths or other food or water supplies for birds. In further embodiments, distributing the composition may involve spraying a liquid or powder composition, or depositing or placing a solid, liquid or powder composition. In certain embodiments, a subject is a bird.

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of any of the ingredients or steps disclosed throughout the specification. Compositions and methods" consisting essentially of any of the ingredients or steps disclosed limits the scope of the claim to the specified materials or steps which do not materially affect the basic and novel characteristic of the claimed invention.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DETAILED DESCRIPTION OF THE INVENTION

Figures 1A, 1B, 1C:
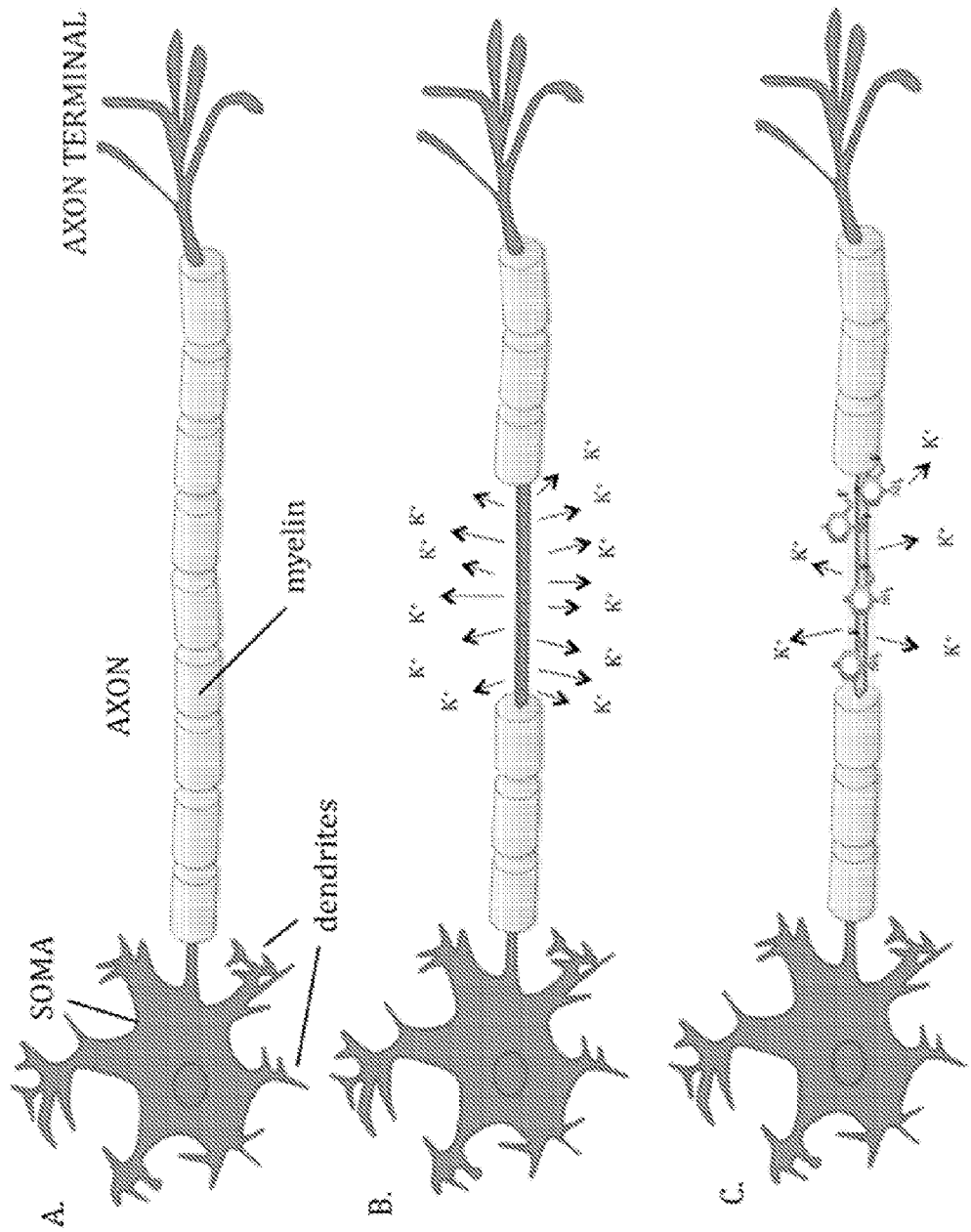
FIGS. 1A-1C illustrate the mechanism of action of a potassium channel blocker. (A) shows a scheme of a healthy neuron. (B) shows a scheme of a demyelinated neuron. Aberrant leakage of potassium ions from the axon results in poor conduction of electrical impulses along the axon. (C) shows a demyelinated neuron treated with a potassium channel blocker.
Figures 2A, 2B, 2C, 2D, 2E, 2F, 2G:
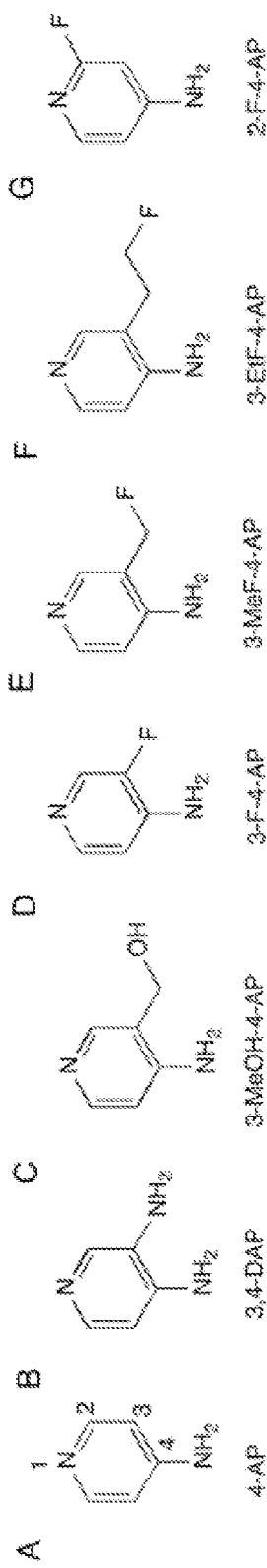
FIGS. 2A-2G show potassium channel blockers and fluorinated 4-AP derivatives. (A) 4-aminopyridine (B) 3,4-diaminopyridine (C) 3-methanol-4-aminopyridine (D) 3-fluoro-4-aminopyridine (E) 3-fluoromethyl-4-aminopyridine (F) 3-fluoroethyl-4-aminopyridine (G) 2-fluoro-4-aminopyridine FIGS. 3A-3F. (A) shows synthesis of 3-fluoromethyl-4-aminopyridine. (B) shows synthesis of 3-fluoroethyl-4-aminopyridine. (C) shows NMR of 3-fluoromethyl-4-aminopyridine. (D) shows high resolution Mass Spectra of 3-fluoromethyl-4-aminopyridine. (E) shows NMR of 3-fluoroethyl-4-aminopyridine. (F) shows high resolution Mass spectra of 3-fluoroethyl-4-aminopyridine.

Multiple sclerosis (MS) is the most common neurodegenerative disease in young adults. The progressive demyelination of neurons in the central nervous system (CNS) is the hallmark of MS (Calabresi, 2007). When axons lose their myelin, $K^+$ channels in the axonal membrane become exposed and leak $K^+$ ions (FIGS. 1A and B). The aberrant leakage of $K^+$ ions from the axons results in poor impulse conduction, which in turn causes the appearance of neurological symptoms (Ritchie et al., 1981; Waxman and Ritchie, 1993; Rasband et al., 1998; Arroyo et al., 2004).

Positron Emission Tomography (PET) allows imaging of molecular changes before macroscopic changes have occurred and therefore it provides an opportunity for early detection. It does this by detecting a radiation coming from a radionuclide introduced in the body in a biologically active molecule that selectively localizes to the area of interest, also known as tracer. Images of the tracer's distribution can be reconstructed using computer analysis allowing precise mapping of its location. For example, $^{18}$F-fludeoxyglucose is widely used to image highly metabolically active cells such as cancer cells inside an organism. Similarly, it is conceivable that a PET-active molecule that selectively localizes to injured areas in the brain could provide accurate maps of TBI.

During TBI, compression or stretching of the brain often causes axons to tear and oligodendrocytes (cells responsible for producing and maintaining myelin) to break. Injury to oligodendrocytes can leave axons devoid of myelin, which then become more sensitive to degeneration. It is well known that loss of myelin (as in conditions like multiple sclerosis, MS) causes $K^+$ channels, which are usually buried beneath the myelin sheath to become exposed and leaky.

4-aminopyridine (4-AP) and 3,4-diaminopyridine (3,4-DAP) are well-known potassium channel blockers relatively selective for voltage gated $K^+$ channels of the $K_v1$ family (Wulff et al., 2009). 4-AP sensitive K+ channels, Kv1.1 and Kv1.2, are localized in the juxtaparanodal region of myelinated axons. Upon demyelination these channels redistribute throughout the intermodal region of the axons as seen in tissue samples from MS patients and in demyelinated animals. In demyelinated animals Kv1 channels have been shown to be upregulated 2-4 fold. 4-AP and 3,4-DAP have been used effectively in the treatment of Lambert-Eaton Syndrome and Multiple Sclerosis (Murray and Newsom-Davis, 1981; Soni and Kam, 1982; Lundh et al., 1977). 4-AP and 3,4-DAP block $K_v1$ potassium channels with affinities in the micromolar range. Binding of 4-AP and 3,4-DAP to $K_v1$ potassium channels restores impulse conduction in demyelinated fibers (Yeh et al., 1976; Sherratt et al., 1980; Kirsch and Narahashi, 1978). 4-aminopyridine-3-methanol can also restore impulse conduction of demyelinated fibers (Sun et al., 2010; Leung et al., 2011).

In 2010, the FDA approved a slow-release formulation of 4-aminopyridine (4-AP), to improve walking in MS patients (Ampyra, Acorda Therapeutics, Inc., 2010). 4-AP is a relatively selective blocker of $K_v1$ family of $K^+$ channels (Wulff et al., 2009). The proposed mechanism of action of 4-AP in MS patients is that 4-AP blocks $K^+$ channels in demyelinated axons, which leads to improved impulse conduction.

Fluorinated molecules generally display better pharmacological properties such as increased membrane permeability and metabolic stability than their non-fluorinated analogs. Described herein are compounds of formula I or II, which contain fluorine and efficiently block voltage gated potassium channels. In particular, certain embodiments are directed to fluorinated 4-AP derivatives, such as 3-fluoromethyl-4-aminopyridine, or 3-fluoroethyl-4-aminopyridine.

In addition, 4-AP can efficiently cross the blood brain barrier. Application of a computational model for the estimation of log BB (a parameter used to predict blood brain barrier permeability by certain compounds) predicts that the compounds described herein, in particular, fluorinated 4-AP derivatives, will efficiently cross the blood brain barrier (Sun, 2004). It has also been shown that 3-F-4-AP is more lipophylic than 4-AP (Arzneimittelforschung, 1989)

4-AP is safe within the concentrations used in therapy, which indicates that the compounds described herein, in particular, fluorinated 4-AP derivatives are likely to be safe tools when used in humans.

To effectively treat a patient with a neurodegenerative disease, such as MS, it is important to diagnose and evaluate the progression of the disease in the patient. Currently, magnetic resonance imaging (MM) is the primary imaging techniques for the diagnosis and the assessment of disorders that disrupt the myelin sheath, including MS. Unfortunately, signal changes on an MM are non-specific and correlate only indirectly with the underlying pathology. Moreover, current methods do not correlate well with the underlying pathology of the disease and are not well-suited for use in clinical trials.

PET is a non-invasive medical imaging technique that relies on the detection of radiation emitted by a radionuclide (radioactive tracer) introduced in the body of the subject on a biologically active molecule. Images of the radioactive tracer's localization can be reconstructed by computer analysis providing quantitative maps of the radioactive tracer's distribution in the body of the subject. Such images can provide valuable information of the biochemistry and physiology of a subject. Because PET is a molecular imaging technique, it can detect cellular abnormalities before anatomical changes have occurred. For example, 18F-fluorodeoxyglucose (FDG) is widely used to distinguish highly metabolically active cancer cells from other cells (Oriuchi et al., 2006). Similarly, it is conceivable that a "PET-active" molecule that selectively localizes to demyelinated axons could provide accurate maps of the lesions early in the process.

The most common radioisotopes used in PET are $^{18}$F, $^{15}$O, $^{13}$N, $^{13}$N and $^{11}$C, with half-lives of 110, 2, 10, and 20 min respectively. $^{18}$F is usually preferred due to its longer half-life and its lower positron energy which results in better resolution. Despite the relatively short half-life of these radioisotopes, they are widely used in medical diagnostics as many hospitals have their own cyclotron to prepare the radioactive tracers or have a nearby facility that can prepare the radioactive tracers.

A recent review on PET markers for MS highlighted several potential targets for PET imaging including 18 kDa Translocator Protein, Cannabinoid Receptor Type 2, Myelin, Cerebral metabolic rate of glucose utilization, Type A γ-aminobutyric acid, and Acetyl choline receptor (Owen et al., 2011). Nevertheless, all of these markers have limitations: some of these tracers were originally developed for other conditions and suffer from low pathological specificity; others were developed to target myelin or myelin related proteins and have limited signal-to-noise ratio and the rest target inflammatory cells which do not necessarily correlate with the underlying demyelination. More recently, a report on [$^{11}$C]PIB, a PET radioactive tracer that binds to amyloid plaques originally developed for Alzheimer's Disease, has been shown to be useful in quantifying myelin (Stankoff et al., 2011). Nevertheless, since MS is a de-myelinating disorder, it would be desirable to have access to a PET radioactive tracer specific for de-myelinated axons. In particular, it would be desirable to develop a PET radioactive tracer that targets potassium channels for imaging demyelination or other conditions.

Incorporation of a positron emitting radionuclide such as $^{18}F$ into a potassium channel blocker, such as a 4-AP derivative, allows visualization of the location and abundance of exposed potassium channels and provides a better assessment of demyelinated regions. The fact that 4-AP has proven therapeutically beneficial indicates that it preferentially binds to potassium channels of demyelinated neurons. Furthermore, the fact that there are relatively few side effects of 4-AP indicates that there are few off-target receptors at the concentrations currently used in therapy. Such properties indicate that the compounds described herein are suitable for imaging demyelinated neurons with adequate signal-to-noise ratio.

Furthermore, the metabolic stability of [$^{18}F$]Fluoroalkylbiphenyls, which share a similar core structure to the compounds described herein, have been examined and were found to be stable for PET studies (Lee et al., 2004), indicating that the compounds described herein are likely stable for PET studies.

Substitution of $^{18}F$ for OH or H is common in the art. Such substitutions generally preserve the biological properties of the molecule and render the molecules suitable for imaging using PET or SPECT cameras. For example substitution of the OH in position 2 of glucose with $^{18}F$ does not alter the capability to be uptaken by cells. Many examples of $^{18}F$ substitutions that preserve the parent molecule's properties can be found on the MICAD database (available on the world wide web at ncbi.nlm.nih.gov/books/NBK5330/).

FIG. 1C shows a cartoon representation of the proposed mechanism of action of the radioactive tracer. 4-AP as well as the radioactive tracers described herein bind to potassium channels on demyelinated axons decreasing efflux of $K^+$. Visualization of the localization of these molecules can inform of the localization and extent of demyelinated axons.

Disclosed herein are new radioactive tracers for PET, which serve as novel diagnostic markers to image demyelinated axons in a subject. In particular embodiments, the new radioactive tracers for PET are $^{18}F$-labeled versions of 4-AP derivatives. Methods for their manufacture and methods for their use in in vivo imaging of the central nervous system to diagnose and/or assess the progression of MS or other diseases are also provided. The present disclosure also provides fluorine containing compounds that bind to potassium channels, methods for their manufacture and methods for their use in the treatment of neurodegenerative diseases.

I. DEFINITIONS

The term "radioactive isotope" refers to an isotope having an unstable nucleus that decomposes spontaneously by emission of a nuclear electron, positron, or helium nucleus and radiation, thus achieving a more stable nuclear composition.

The term "deuterated version" as used herein means one or more of hydrogen in a compound is replaced with $^2H$, an isotope of hydrogen.

As used herein, the term "radioactive tracer", or "radioactive label", or "tracer", or "radiotracer" means a chemical compound in which one or more atoms have been replaced by a radioisotope. By virtue of its radioactivity, it can be used to explore the mechanism of chemical reactions by tracing the path that the radioisotope follows from reactants to products. A radioactive tracer can also be used to track the distribution of a substance within a natural system such as a cell or tissue. Radioactive tracers form the basis of a variety of imaging systems, such as PET scans and SPECT scans.

The use of the word "a" or "an," when used in conjunction with the term "comprising" in the claims and/or the specification may mean "one," but it is also consistent with the meaning of "one or more," "at least one," and "one or more than one."

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. COMPOUNDS THAT BLOCK POTASSIUM CHANNELS

Certain embodiments provide compounds that block potassium channels having the following formula:

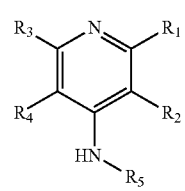

wherein $R_1$, $R_2$, $R_3$, and $R_4$ are independently selected from the group consisting of H, $(CH_2)_nX$, $CH_2OCH_2CH_2X$, $NH_2$, $CH_2OH$, and $CF_3$, and $R_5$ is selected from the group consisting of H, $(CH_2)_mX$, and OH, wherein n=0, 1, 2, 3, 4, or 5, and m=2, 3, 4, or 5; wherein X represents a fluorine atom or an isotope thereof; wherein at least one of $R_1$, $R_2$, $R_3$, $R_4$ and $R_5$ is not hydrogen; wherein at least one of $R_1$, $R_2$, $R_3$, $R_4$ and $R_5$ contains a fluorine atom or an isotope thereof; wherein when $R_2$ is $NH_2$ or $CH_2OH$ or a nonradioactive fluorine or $CF_3$, at least one of $R_1$, $R_3$, $R_4$, and $R_5$ is not hydrogen; wherein when $R_4$ is $NH_2$, $CH_2OH$, a nonradioactive fluorine, or $CF_3$, at least one of $R_1$, $R_2$, $R_4$, and $R_5$ is not hydrogen; and wherein any of C, N, O is optionally replaced by the isotope $^{11}C$, $^{13}N$, $^{15}O$, respectively, or a pharmaceutical acceptable salt thereof, a tautomer thereof or a deuterated version thereof.

In some embodiments, the compounds have the formulas found in FIGS. 2A-G. In particular embodiments, the compounds have the formulas of FIG. 2E and FIG. 2F, which are not commercially available and have never been described before.

In further embodiments, 4-AP derivatives having the following formula are provided:

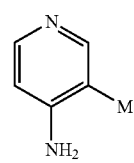

wherein M is $(CH_2)_nY$, and wherein n=0, 1, or 2, and Y is fluorine or an isotope thereof.

In certain embodiments, there are provided compounds of formula (III):

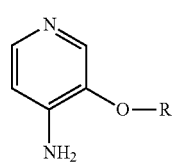

wherein R is selected from the group consisting of $CH_3$, $CH_2F$, $CHF_2$, and $CF_3$, and wherein C is substituted by $^{11}C$ or at least one of F is substituted by $^{18}F$ in R.

Further embodiments are directed to the compounds of formula (IV):

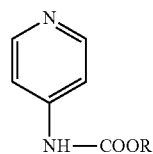 (IV)

wherein R is selected from the group consisting of $CF_3$, $CH_2F$, $CH_3CH_2F$, $C(CH_3)_3$, and wherein at least one of F or H in the R group is substituted by $^{18}F$.

The compounds provided by the present disclosure are described in the summary of the invention section and in the claims below.

Compounds employed in methods described herein may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The compounds can be formulated as a mixture of one or more diastereomers. Alternatively, the diastereomers can be separated and one or more of the diastereomers can be formulated individually. The chiral centers of the compounds disclosed herein can have the S or the R configuration, as defined by the IUPAC 1974 Recommendations. For example, mixtures of stereoisomers may be separated using techniques known to those of skill in the art.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutical research. Isotopes, as used herein, include those atoms having the same atomic number but different mass numbers. By way of general example and without limitation, isotopes of hydrogen include deuterium and tritium, and isotopes of carbon include $^{11}C$, $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds disclosed herein may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, certain embodiments contemplate prodrugs of compounds described herein as well as methods of delivering prodrugs. Prodrugs of the compounds may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

The compounds described herein may exist in unsolvated forms as well as solvated forms, including hydrated forms. In general, the solvated forms are equivalent to unsolvated forms and are within the scope of the compounds described herein. The compounds described herein may exist in multiple crystalline or amorphous forms. In general, all physical forms are equivalent for the uses described herein and are intended to be within the scope of the compounds described herein.

Compounds provided herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. FORMULATIONS

The compounds described herein can be formulated for enteral, parenteral, topical, or pulmonary administration. In other embodiments, the formulation is for administration to a subject, but it may not be directly to the subject. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, sub conjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Formulations may be stable over a period of 6 months when stored at room temperature or 4° C.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references such as "Pharmaceutical dosage form tablets" (1989), "Remington—The science and practice of pharmacy" (2000), and "Pharmaceutical dosage forms and drug delivery systems" (1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more 4-AP derivatives and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more 4-AP derivatives and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more 4-AP derivatives, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the 4-AP derivatives and/or additional active agents.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof.

D. Other Formulations

Any of the formulations discussed above may be used for a formulation that is not a pharmaceutical formulation. In some embodiments, a formulation may be prepared for administration to a subject by a method that is direct or by a method that is indirect. In certain embodiments, a compound is provided in a liquid, solid, or powder formulation. The compound may be in a composition that is sprayed or otherwise applied to a surface or location. In some embodiments, the composition is placed in a location that is accessible to the subject so that the subject ingests or comes into contact with the composition. In certain embodiments, the compound is absorbed or adsorbed by the subject.

IV. METHODS OF MAKING COMPOUNDS THAT BLOCK POTASSIUM CHANNELS

The compounds provided by the present disclosure are described in the summary of the invention section and in the claims below. They may be made using the methods outlined in the summary of the invention section and in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The compounds or compositions described herein can also be prepared by any of the applicable techniques of organic synthesis and polymer chemistry. Many such techniques are well known in the art. Many of the known techniques are elaborated in Compendium of Organic Synthetic Methods, Vol 1, 1971; Vol. 2, 1974; Vol. 3, 1977; Vol. 4, 1980; Vol. 5, 1984; and Vol. 6, 1985; Comprehensive Organic Synthesis Selectivity, Strategy & Efficiency in Modern Organic Chemistry, 1993; Advanced Organic Chemistry, Part B: Reactions and Synthesis, $4^{th}$ Ed., 2001; Advanced Organic Chemistry, Reactions, Mechanisms, and Structure, $2^{nd}$ Ed., 1977; Protecting Groups in Organic Synthesis, $2^{nd}$ Ed., 991; Comprehensive Organic Transformations, $2^{nd}$ Ed., 1999, Textbook of Polymer Chemistry, $3^{rd}$ Ed., 1984, Organic Polymer Chemistry, $2^{nd}$ Ed., 1973, and Polymer Science, 1986. These are incorporated herein by reference.

V. METHODS OF USING COMPOUNDS THAT BLOCK POTASSIUM CHANNELS

A. Treatment

The compounds described herein can be administered to provide an effective amount to prevent, treat or mitigate a symptom of a variety of diseases and disorders, in particular, a disease associated with demyelination, such as multiple sclerosis. The compounds described herein can be administered to a subject in need thereof to treat the subject either prophylactically (e.g., to prevent a demyelination disease) or therapeutically (e.g., to treat a demyelination disease after it has been detected), including, but not limited to, ameliorating the symptoms of a disease, reducing the pain of the patient, delaying the progression of the disease, preventing new attacks or recurring of the disease, preventing disability and/or increasing survival time of the patient.

The compounds described herein can bind to potassium channels, such as Kv1 potassium channels located in the axonal membrane to partially or completely restore the impulse conduction along the axon. In some embodiments, the compounds described herein may also be used to treat non-neurological diseases when blocking of potassium channels in the heart or other tissues expressing potassium channels is desired.

By administering the compounds described herein to a patient suffering from a demyelinating disease, one or more symptoms associated with demyelination may be mitigated or eliminated. The symptoms include changes in sensation such as loss of sensitivity or tingling, pricking or numbness (hypoesthesia and paresthesia), muscle weakness, clonus, muscle spasms, or difficulty in moving; difficulties with coordination and balance (ataxia); problems in speech (dysarthria) or swallowing (dysphagia), visual problems (nystagmus, optic neuritis including phosphenes, or diplopia), fatigue, acute or chronic pain, and bladder and bowel difficulties. The symptoms may further include cognitive impairment of varying degrees and emotional symptoms of depression or unstable mood are also common, Uhthoff's phenomenon, an exacerbation of extant symptoms due to an exposure to higher than usual ambient temperatures, and Lhermitte's sign, an electrical sensation that runs down the back when bending the neck.

Exemplary demyelination diseases which can be treated by the compounds described herein include, but are not limited to, multiple sclerosis, spinal cord compression, ischemia, acute disseminated encephalomyelitis, optic neuromyelitis, leukodystrophy, progressive multifocal leukoencephalopathy, metabolic disorders, toxic exposure, congenital demyelinating disease, peripheral neuropathy, encephalomyelitis, central pontine myelolysis, Anti-MAG Disease, Guillain-Barre syndrome, chronic inflammatory demyelinating polyneuropathy, or multifocal motor neuropathy (MMN). Exemplary leukodystrophy includes, but is not limited to adrenoleukodystrophy, Alexander's Disease, Canavan Disease, Krabbe Disease, Metachromatic Leukodystrophy, Pelizaeus-Merzbacher Disease, vanishing white matter disease, Refsum Disease, Cockayne Syndrome, Van der Knapp Syndrome, or Zellweger Syndrome.

Patients can be treated using a variety of routes of administration including systemic administration, such as intravenous administration or subcutaneous administration, oral administration or by intratumoral injection.

In certain embodiments, it may be desirable to provide continuous delivery of one or more compounds described herein to a patient in need thereof. For intravenous or intraarterial routes, this can be accomplished using drip systems, such as by intravenous administration. For topical applications, repeated application can be done or a patch can be used to provide continuous administration of the compounds described herein, including 4-AP derivatives over an extended period of time. Extended release formulations can also be used to provide limited but stable amounts of the drug over an extended period of time.

For internal applications, continuous perfusion of the region of interest may be desirable. This could be accomplished by catheterization, post-operatively in some cases, followed by continuous administration of the one or more 4-AP derivatives. The time period for perfusion can be readily determined by the attending physician clinician for a particular subject. Perfusion times typically range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered.

The compositions described herein contain an effective amount of the one or more compounds described herein. The amount to be administered can be readily determined by the attending physician based on a variety of factors including, but not limited to, age of the patient, weight of the patient, disease or disorder to be treated, presence of a pre-existing condition, and dosage form to be administered (e.g., immediate release versus modified release dosage form). Typically, the effective amount is from about 0.01 mg/kg/day to about 100 mg/kg/day, from 0.1 mg/kg/day to 50 mg/kg/day, from 0.1 mg/kg/day to 25 mg/kg/day, 0.1 mg/kg/day to 10 mg/kg/day, from 0.1 mg/kg/day to 1 mg/kg/day or any range derivable therein. Dosages greater or less than this may be administered depending on the diseases or disorder to be treated.

The therapeutically effective doses could also be determined by using an animal model. For example, a mouse bearing experimental autoimmune encephalomyelitis (EAE) could be used to optimize appropriate therapeutic doses prior to translating to a clinical environment.

The therapeutically effective doses could also be determined by using an animal model. For example, a rodent bearing Traumatic Brain Injury could be used to optimize appropriate therapeutic doses prior to translating to a clinical environment.

In some embodiments, the compounds and compositions disclosed herein may be useful in a variety of manners. In some embodiments, the compounds and compositions disclosed herein may be useful for improving gait in stroke patients. In some embodiments, the compounds and compositions disclosed herein may be useful in research to induce seizures. In some embodiments, the compounds and compositions disclosed herein may be useful as pest control agents. In some embodiments, the compounds and compositions disclosed herein may be useful for Parkinson's Disease, pediatric and adult Cerebral Palsy, Spinal Cord Injury, Lambert Eaton syndrome, and MS.

In some embodiments, derivatives of 4-AP will have improved pharmacological properties over 4-AP. 3-F-4-AP has better permeability into the CNS than 4-AP and, therefore, it may be better for CNS diseases. Fluorinated 4-APs may have longer half life than 4-AP, may be less toxic, and may be more stable to metabolic degradation.

B. Imaging

The compounds described herein can also be used as imaging agents in medical imaging applications. Medical imaging is the technique and process used to create images of the human body (or parts and function thereof) for clinical purposes (medical procedures seeking to reveal, diagnose or examine disease) or medical science (including the study of normal anatomy and physiology). Medical imaging may also be applied to an animal body. Commonly used medical imaging techniques include, but are not limited to, radiography, magnetic resonance imaging (MRI), fiduciary markers, nuclear medicine, photo acoustic imaging, breast thermography, tomography, and ultrasound.

1. Radiography

Projection radiograph, also known as x-rays, and fluoroscopy are two forms of radiographic images used in medical imaging; with the latter being useful for catheter guidance. This imaging modality utilizes a wide beam of x rays for image acquisition and is the first imaging technique available in modern medicine.

2. Magnetic Resonance Imaging (MRI)

Magnetic resonance imaging instrument (MRI scanner), or "nuclear magnetic resonance (NMR) imaging" scanner as it was originally known, uses powerful magnets to polarise and excite hydrogen nuclei (single proton) in water molecules in human tissue, producing a detectable signal which is spatially encoded, resulting in images of the body.

3. Fiduciary Markers

Fiduciary markers are used in a wide range of medical imaging applications. Images of the same subject produced with two different imaging systems may be correlated (called image registration) by placing a fiduciary marker in the area imaged by both systems. In this case, a marker which is visible in the images produced by both imaging modalities must be used.

4. Nuclear medicine

Nuclear medicine encompasses both diagnostic imaging and treatment of disease. Nuclear medicine uses certain properties of isotopes and the energetic particles emitted from radioactive material to diagnose or treat various pathology. This approach is often used in e.g., scintigraphy, SPECT and PET to detect regions of biologic activity that may be associated with disease. Isotopes are often preferentially absorbed by biologically active tissue in the body, and can be used to identify tumors or fracture points in bone. Images are acquired after collimated photons are detected by a crystal that gives off a light signal, which is in turn amplified and converted into count data.

Scintigraphy ("scint") is a form of diagnostic test wherein radioisotopes are taken internally, for example intravenously or orally. Then, gamma cameras capture and form two-dimensional images from the radiation emitted by the radiopharmaceuticals.

SPECT is a 3D tomographic technique that uses gamma camera data from many projections and can be reconstructed in different planes. In SPECT imaging, the patient is injected with a radioisotope, most commonly Thallium 201TI, Technetium 99mTC, Iodine 123I, and Gallium 67Ga.

Positron emission tomography (PET) uses coincidence detection to image functional processes. Short-lived positron emitting isotopes, such as $^{18}$F, are incorporated with an organic substance such as glucose, creating F18-fluorodeoxyglucose, which can be used as a marker of metabolic utilization. Images of activity distribution throughout the body can show rapidly growing tissue, like tumor, metastasis, or infection. PET images can be viewed in comparison to computed tomography scans to determine an anatomic correlate. Modern scanners combine PET with a CT, or even MM, to optimize the image reconstruction involved with positron imaging. This is performed on the same equipment without physically moving the patient off of the gantry. The resultant hybrid of functional and anatomic imaging information is a useful tool in non-invasive diagnosis and patient management.

5. Tomography

Tomography is the method of imaging a single plane, or slice, of an object resulting in a tomogram. There are several forms of tomography, including linear tomography, poly tomography, zonography, orthopantomograph (OPT or OPG), and computed tomography (CT).

6. Ultrasound

Medical ultrasonography uses high frequency broadband sound waves in the megahertz range that are reflected by tissue to varying degrees to produce (up to 3D) images. This is commonly associated with imaging the fetus in pregnant women. Uses of ultrasound are much broader, however. Other important uses include imaging the abdominal organs, heart, breast, muscles, tendons, arteries and veins.

In certain embodiments, the compounds described herein are used for in vivo imaging of the central nervous system. More specifically, the compounds described herein bind to potassium channels, including Kv1 channels. The compounds disclosed herein contain one or more radioisotopes. Exemplary radioisotopes include, but are not limited to, $^{18}$F, $^{11}$C, $^{13}$N, and $^{15}$O. It would be within an artisan's ordinary skill to choose appropriate radioisotope suitable for the imaging technique intended to use. In some embodiments, one or more imaging techniques may be combined for imaging purposes. For example, PET may be combined with MM. In some aspects, PET is used to image demyelination and MM is used to image inflammation. PET and MRI are complement to each other and can provide valuable information on progression of the MS disease in a patient.

One particular embodiment is directed to radiolabelled 4-AP derivatives that target potassium channels of demyelinated neurons. These radiotracers may be used as in vivo imaging agents for demyelination. In particular embodiments, these radiotracers are suitable for PET imaging technique. In one embodiment, the radiotracers described herein contain $^{18}$F.

Since the compounds described herein are capable of blocking potassium channels, such as Kv1 potassium channels located in the axonal membrane, the use of [$^{18}$F]-labeled 4-AP derivatives such as [$^{18}$F]-fluoromethyl-4-aminopyridine, or [$^{18}$F]-3-fluoro-4-aminopyridine, or other radiotracers described herein allows visualization of demyelinated axons in live animals by proper medical imaging techniques, such as PET. Therefore, the compounds described herein may be used to diagnose a demyelinating disease or assessing the progression of a demyelinating disease by administering the compounds to a subject in need thereof and detecting the compounds in the subject by proper medical imaging technique, such as PET, PET-Time-Activity Curve (TAC), PET-MRI, in particular, PET. In some embodiments, one or more medical imaging techniques disclosed herein may be used to diagnose or evaluate the progression of a disease.

VI. KITS

In various aspects, a kit is envisioned containing one or more compounds described herein. The kit may contain one or more sealed containers, such as a vial, containing any of the compounds described herein and/or reagents for preparing any of the compounds described herein. In some embodiments, the kit may also contain a suitable container means, which is a container that will not react with components of the kit, such as an Eppendorf tube, an assay plate, a syringe, a bottle, or a tube. The container may be made from sterilizable materials such as plastic or glass.

The kit may further include instructions that outline the procedural steps for methods of treatment or prevention of disease, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of one or more compounds described herein.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the claims.

Example 1. Synthesis of Fluorinated Derivative of 4-AP

4-AP (FIG. 2A) is a relatively specific blocker of voltage-gated K$^+$ channels (K$_v$1 family). 4-AP is a membrane permeable molecule that binds to the intracellular mouth of the K$^+$ channel blocking ionic currents (Sherratt et al., 1980). In demyelinated axons these channels are exposed and easily accessible to the drug. For this reason, the inventors believe that labeling 4-AP with a positron emitting radionuclide will enable imaging of demyelinated regions.

Furthermore, since Kv1 channels are upregulated 2-4 fold in demyelinated animals such as shiverer mice and upregulation of Kv1 channels in demyelinated axons suggests greater signal, the inventors expect that the signal proceeding from demyelinated axons will be greater.

A common approach in the design of PET radioactive tracers is to replace a hydrogen (H), hydroxyl (OH) or methyl (CH$_3$) group with fluorine-18 (Ametamey et al., 2008). Fluorine-18 is the preferred radionuclide due to its low positron energy and its longer half-life. The low positron energy gives it greater spatial resolution and its longer half-life facilitates off-site production and distribution.

In an effort to design 4-AP derivatives that maintain activity and are suitable for PET imaging, the inventors began by examining 4-AP derivatives that are known to block K$^+$ channels. 4-AP (FIG. 2A) and 3,4-diaminopyridine (FIG. 2B), are well-known K$^+$ channel blockers discovered in the 1970's (Sherratt et al., 1980; Kirsch and Narahashi, 1978). More recently Shi et al described 3-methanol-4-aminopyridine (FIG. 2C) as a novel K$^+$ channel blocker (Sun et al., 2010; Leung et al., 2011). From these structures, it appears that some variation is permitted on the 3 position of the pyridine ring. It has also been suggested that certain variations on the 4 position of the pyridine 4 appear to be acceptable as well (Smith et al., 2005). Thus, the inventors hypothesized that 3-fluoro-4-aminopyridine (FIG. 2D), 3-fluoromethyl-4-aminopyridine (FIG. 2E) and 3-fluoroethyl-4-aminopyridine (FIG. 2F) could be suitable K$^+$ channel blockers. These structures (FIGS. 2D-2F) contain different substitutions on position 3 of the pyridine ring which does not alter its function. The inventors also proposed that compound 2-fluoro-4-aminopyridine (FIG. 2G) could also bind to K$^+$ channels.

Figures 3A, 3B:
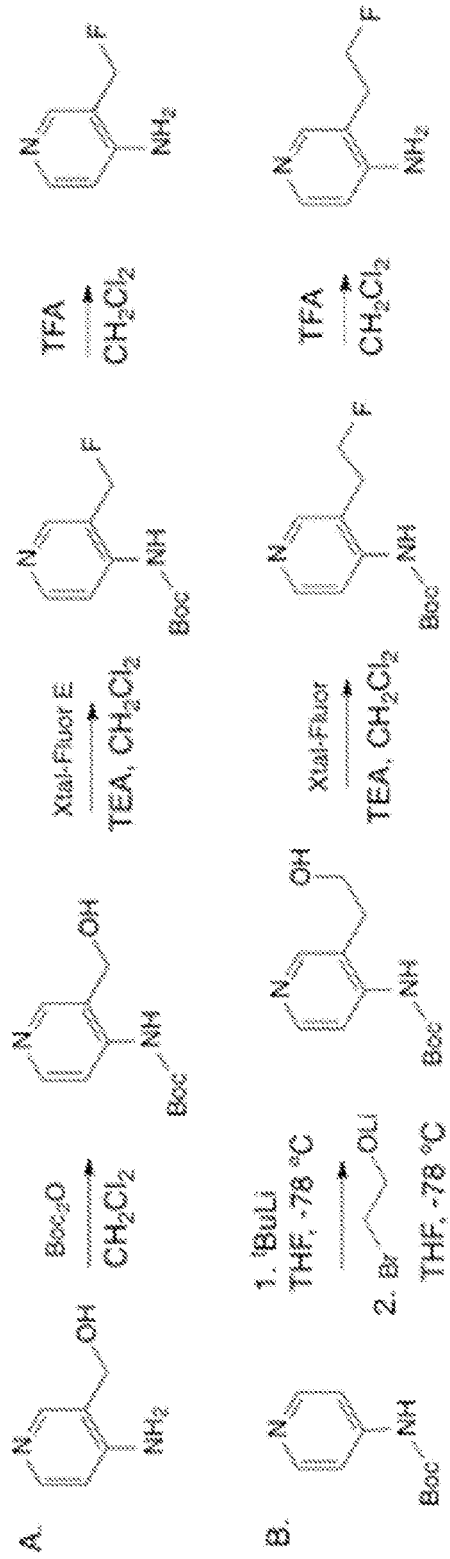
Figure 3C:
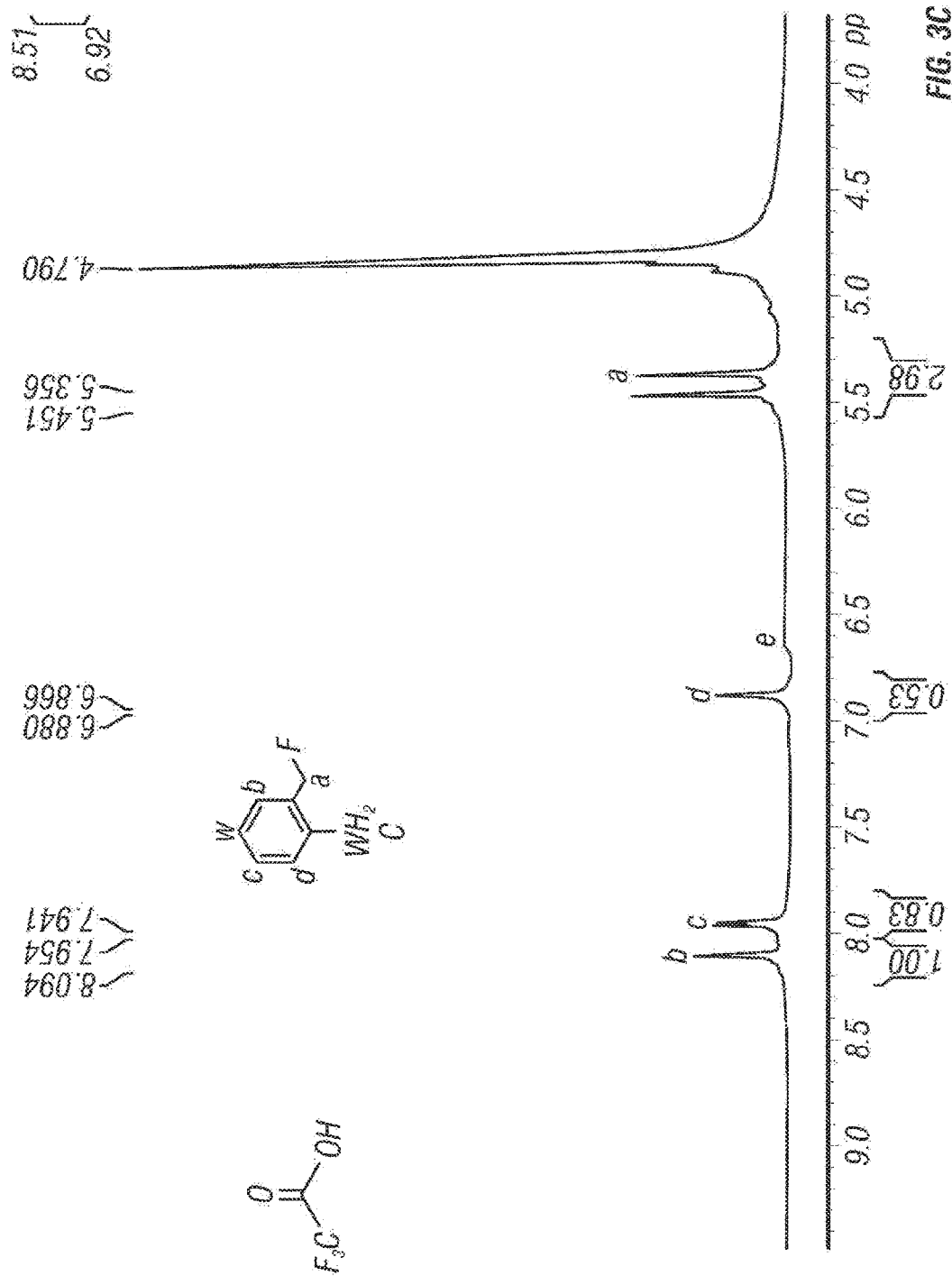
Figure 3D:
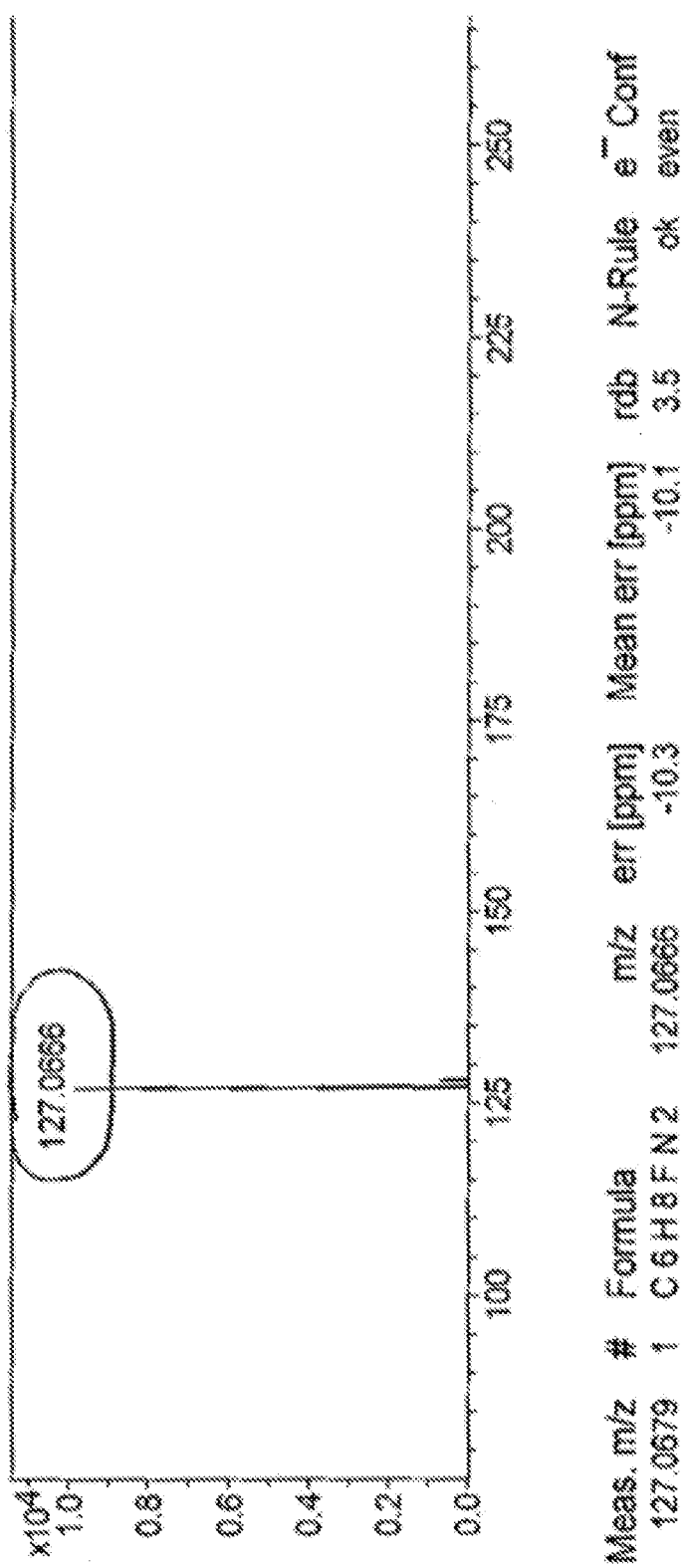
Figure 3E:
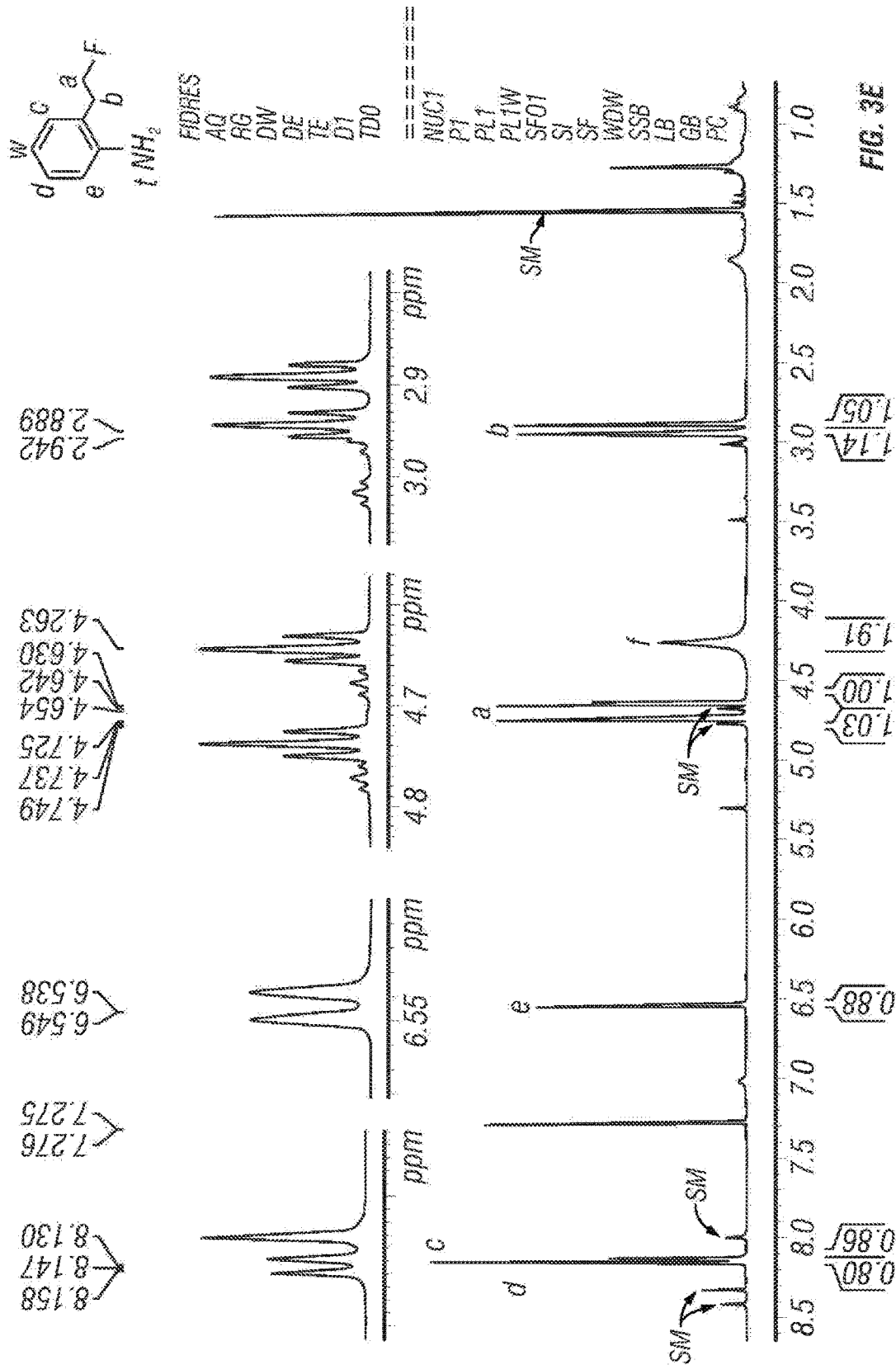
Figure 3F:
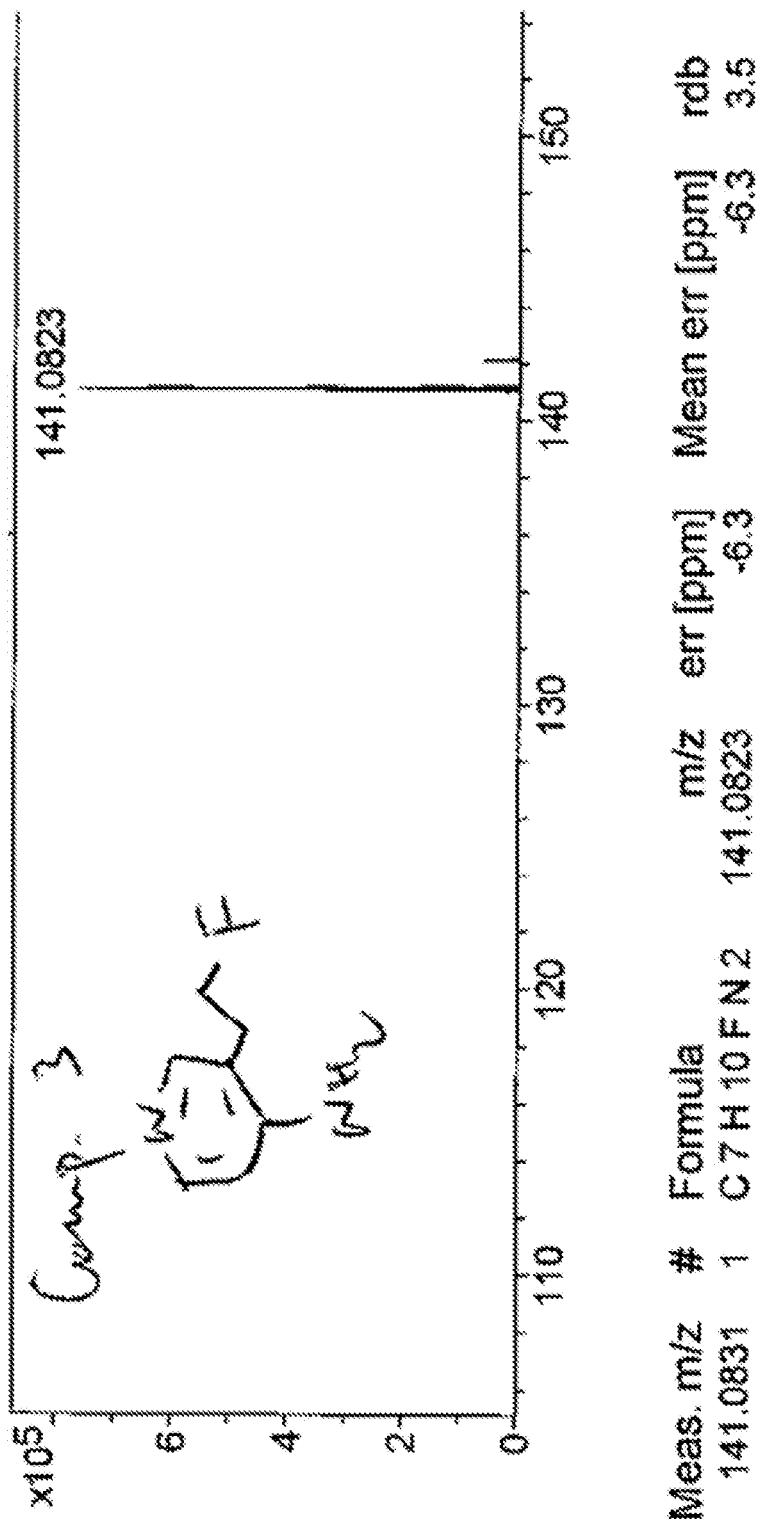

Before radioactive labeling, it is important to test whether these fluorinated derivatives are still able to bind to K$^+$ channels. Non-radioactive 3-fluoro-4-aminopyridine (FIG. 2D) is commercially available from Sigma. Synthesis of fluorinated pyridines which share a core structure similar to the compounds described herein has been reported previously (Lee and Chi, 1999; Mobinikhaledi and Foroughifar, 2006). However, 3-fluoromethyl-4-aminopyridine (FIG. 2E) and 3-fluoroethyl-4-aminopyridine (FIG. 2F) have never been made before. These compounds were synthesized according to syntheses outlined in FIGS. 3A-3B. The production of final products 3-fluoromethyl-4-aminopyridine and 3-fluoroethyl-4-aminopyridine are verified by NMR (FIG. 3C, 3E) and high resolution Mass Spectra (FIG. 3D, 3F), respectively.

Example 2. Confirm Binding to Potassium Channels

Figures 5A, 5B, 5C:
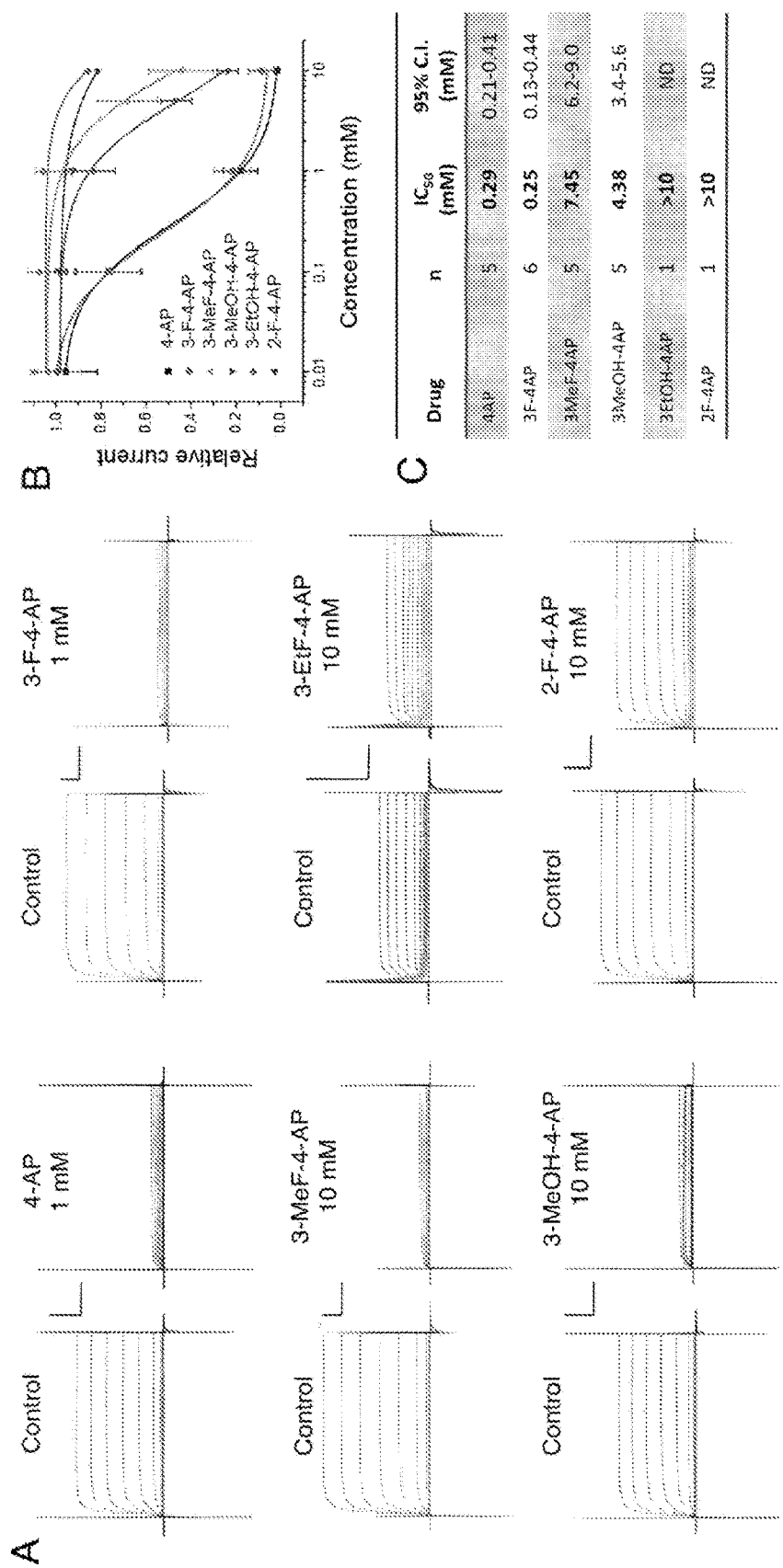
FIGS. 5A-5C show inhibition of ionic current of Shaker $K^+$ channel by 4-AP derivatives. (A) $K^+$ currents were generated by a series of 50 ms pulses from $-70$ mV to $+40$ mV in increments of 10 mV in the presence of cumulative concentrations of 4-AP derivatives. Each panel represents the $K^+$ current recorded from the same oocyte before and after addition of the drug. Scale bar: 1 $\mu$A/10 ms. (B) Relative $K^+$ current vs. concentration for each drug obtained at $+20$ mV. (C) Half-maximal inhibitory concentration of each molecule and 95% confidence interval obtained from fitting the data to the Hill equation. n=number of times each drug was tested.

In order to confirm that the fluorinated 4-AP derivatives maintain the ability to block K$^+$ channels and select the most suitable compound for imaging studies, the inventors measured inhibition of K$^+$ currents in Shaker channels (K$_v$1.2) using cut-open oocyte voltage clamp (Stefani and Bezanilla, 1998) (FIGS. 5A-5B). Using the cut-open oocyte voltage clamp studies to screen compounds to determine their potency towards Kv1 cannels was previously described in Starace and Bezanilla et al. (2004).

Remarkably, 3-fluoro-4-aminopyridine (3F-4AP) has very similar affinity to 4-AP for K⁺ channels. 3-fluoromethyl-4-aminopyridine (3MeF-4AP) is similar to 3-methanol-4-aminopyridine (3MeOH-4AP) and around 10-fold less potent than 4-AP. 3-fluoroethyl-4-aminopyridine (3EtF-4AP) and 2-fluoro-4-aminopyridine (2F-4AP) are at least a hundred fold-less potent than 4-AP. Based on these results, 3F-4AP and 3-MeF-4AP are the preferred molecules for imaging and therapy.

One advantage of 4-AP, and presumably of its analogs, is that they bind to all channels from the $K_v1$ family. It is known that neurons express several of these channels ($K_v1.1$, $K_v1.2$, $K_v1.4$, $K_v1.5$, $K_v1.6$, $K_v1.7$ and $K_v1.8$, among which the most important neuronal voltage gated K+ channels are Kv1.1 and Kv1.2) and that these channels can form hererotetramers. However, it is unclear which one or several are responsible for the aberrant efflux of K⁺ ions from demyelinated axons and thus, a broad-spectrum channel may be beneficial.

A desired property for radioactive tracers is high affinity. It is striking that 4-AP and 3,4-diaminopyridine possess a relatively modest affinity to K⁺ channels (μM to mM) and yet that they are useful in therapeutics (Murray and Newsom-Davis, 1981; Maddison and Newsom-Davis, 2003; Goodman et al., 2009). It is possible that these molecules have a higher effective affinity in vivo as they bind quasi-irreversibly to the channel. Once bound to the channel these molecules become trapped inside the channel and do not dissociate. Thus, it is expected that despite their modest affinity, the PET markers described herein will display a high signal-to-noise ratio.

It is important to note that even though the in vitro affinity of 4-AP is low (~250 μM), 4-AP is active at much lower concentrations in vivo (~0.5 μM). This difference might be because blockage of a small fraction of channels already leads to an effect and because 4-AP binds to the channels when they are open and once the channels close, 4-AP becomes trapped inside, functioning as a non-reversible ligand (Armstrong and Loboda, 2001).

Example 3. In Vivo Effects of Fluorinated 4-AP Derivative

A consequence of excessive K⁺ channel blockage is the advent of seizures. 4-AP is known to cause seizures in mice at high doses. The inventors tested some 4-AP derivatives described herein and compared them to 4-AP in their ability to cause seizures (Table 1).

The fact that only the molecules that are active by cut-open voltage clamp are able to cause seizures strongly suggests that these molecules are targeting K+ channels receptors in vivo.

In addition, the inventors noticed that Shiverer mice, which harbor a mutation on myelin basic protein and suffer from demyelination of the CNS, appear to be less sensitive to 4-AP induced seizures. Previous studies have shown that Shiverers and other demyelinated mice display an abnormal localization pattern $K_v1$ of channels and a 2-4 fold increase in expression of $K_v1.1$ and $K_v1.2$ channels in axons (Wang et al., 1995). The inventors believe that the higher expression of $K_v1$ channels in Shiverer mice is the reason for why these animals are less sensitive to 4-AP. It is not known whether $K_v1$ channels are also upregulated in MS patients, but it is known that $K_v1$ channels in MS lesions present a similar localization patterns as in demyelinated animals (Coman et al., 2006). Therefore, similar upregulation is anticipated. Accordingly, upregulation of $K_v1$ channels in MS patient lesions combined with the presumed lower accessibility of 4-AP to $K_v1$ channels in myelinated axons make $K_v1$ channels an attractive target for PET imaging.

At high doses, 4-AP causes tremors, muscle spasms and seizures. A summary of the observations is shown in Table 1.

TABLE 1

Effects after intraperitoneal injection of 4-AP derivatives (100 μL per 10 g of mouse)

| Drug | MW g/mol | Dose μmol/kg | Dose mg/kg | Effect |
|---|---|---|---|---|
| 4-AP | 94.11 | 30 | 2.82 | Mild tremor, mouse quiet |
|  |  | 60 | 5.65 | Severe tremor, mild jerks, salivation |
|  |  | 90 | 8.47 | Severe tremors and seizures that start 10 min post-injection and last ca. 2 h |
| 3-F-4-AP | 112.11 | 30 | 3.36 | Mouse quiet |
|  |  | 60 | 6.73 | Mild tremor, mouse quiet |
|  |  | 90 | 10.1 | Severe tremors and seizures that start 10 s post-injection and last ca. 30 min. 1 of 5 mice died of seizure |
|  |  | 30 | 3.78 | No effect |
|  |  | 60 | 7.57 | Very mild tremor. Normal after 30 min |
| 3-MeF-4-AP | 126.13 | 90 | 11.4 | Tremor and occasional jerks that last ca. 45 min |
|  |  | 120 | 15.1 | Severe tremor and seizures that start 5 min post-injection and last ca. 45 min. 1 of 5 mice died of seizure |
| 3-MeOH-4-AP | 124.14 | 960 | 119.1 | No effect |
| 2-F-4-AP | 112.11 | 1920 | 215.2 | No effect |

N = 5 per group.

From this experiment it can be seen that 3-F-4-AP and 3-MeF-4-AP have very similar effects as 4-AP in mice. Both of these drugs cause salivation, tremors, jerks, extension of the hind limbs and seizures. 3-F-4-AP has very similar potency to that of 4-AP and acts much faster (onset of seizures at highest dose 10 s vs. 10 min) which is consistent with a faster absorption and a higher permeation of the blood-brain barrier. 3-MeF-4-AP is slightly less potent than 4-AP but remarkably potent considering that in the voltage-clamp and optic nerve experiments it was found to be 6-20 times less potent than 4-AP. In contrast, 2-F-4-AP and 3-MeOH-4-AP did not cause any effects at doses up to 20 times higher. The inventors also tested the effect of the drugs given by oral gavage on a small number of animals and found the same effects (data not shown).

Example 4 (Prophetic Example). Synthesis of [$^{18}$F] 4-Amino-3-(Fluoromethyl)Pyridine

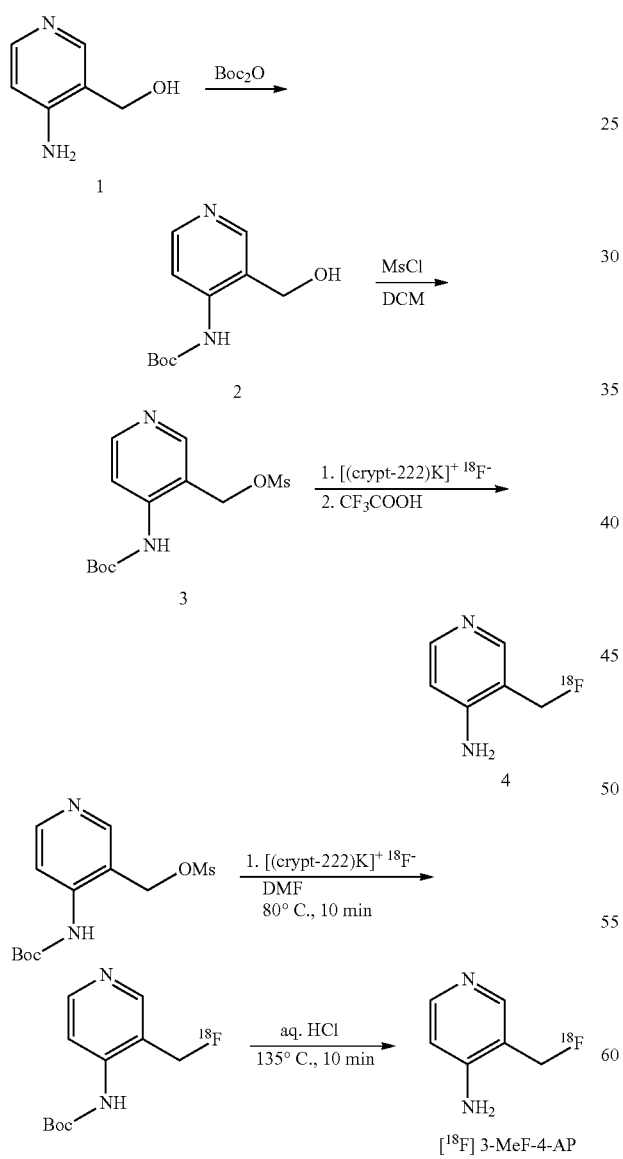

Based on the report by Lee et al on the synthesis of fluoroalkyl pyridines with fluorine-18 (Lee et al., 1999), this example depicts a possible synthetic route to generate [$^{18}$F]-3-fluoromethyl-4-aminopyridine by protecting the amine of 4-aminopyridine-3-methanol with Boc, followed by nucleophilic substitution of the benzyl alcohol with $^{18}$F$^-$, and boc deprotection.

A solution of Boc$_2$O (0.20 mol) in CH$_2$Cl$_2$ (100 mL, not anhydrous) is added over 20 min to a stirred suspension of 4-aminopyridine-3-methanol (0.20 mol) in CH$_2$Cl$_2$ (200 mL). The resulting solution is stirred at room temperature for 25 min (TLC) and acidified with 1 M HCl (230 mL, 0.23 mol). The phases are separated, and the aqueous layer is washed with CH$_2$Cl$_2$. The combined organic extracts are dried (MgSO$_4$) and evaporated in vacuum to give compound 2 which is used in the next step without further purification.

$^{18}$F water is added to the reaction vessel followed by [$^{18}$F$^-$] K222 (2 mg) in acetonitrile (500 ml), and K$_2$CO$_3$ (0.1 mol dm$^{-3}$, 50 ml) and dried at 100° C. for 20-30 min. Compound 3 (1 mg) in acetonitrile (1000 mL) is added. The reaction vessel is sealed and heated at 100° C. for 10 min. The reaction mixture is cooled, washed from the reaction vessel with water (1.5 mL) and collected in a vial. 3 mL of CF$_3$COOH are added to the vial and the reaction is heated in a microwave (75 W, 140° C.) for 3 min. Subsequently, the reaction mixture is purified by reverse phase HPLC. Finally, the fractions containing the product are diluted to 5 mL in PBS.

Example 5 (Prophetic Example). Synthesis of [$^{18}$F] 4-Amino-3-(Fluoroethyl)Pyridine

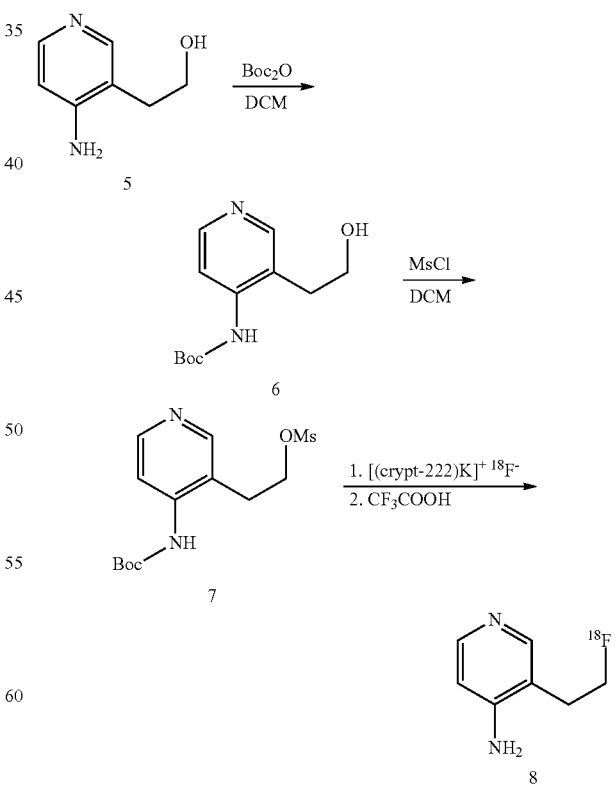

The synthesis of compound 8 starting from compound 5 may be performed using the same procedure to Example 4.

Example 6 (Prophetic Example). Synthesis of [$^{18}$F] 4-Amino-3-Fluoropyridine

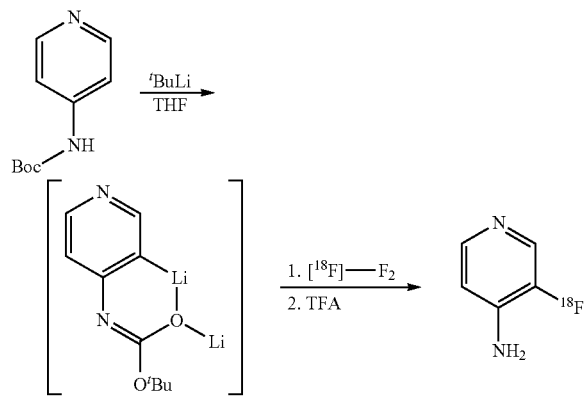

This example depicts a possible synthetic route to generate [$^{18}$F]-3-fluoro-4-aminopyridine by double deprotonation of N-boc protected 4-aminopyridine followed by reaction with [$^{18}$F]—F$_2$ and Boc deprotection. Other synthesis including using the recently reported Pd-mediated electrophilic synthesis (Lee et al., 2011) may also be applicable for synthesizing [$^{18}$F]-3-fluoro-4-aminopyridine.

To a solution of 9 (200 mmol) in THF (500 mL) at −78° C. is added t-BuLi (282 mL, 1.7 M, 480 mmol) in pentane over 70 min. The resulting bright yellow suspension is stirred at −78° C. for 20 min and at −15° C. for 2 h. Subsequently, [$^{18}$F]—F$_2$ is bubbled through 5 ml of solution containing lithiated species 10. After 20 min, 3 mL of CF$_3$COOH are added to the solution and the reaction is heated in a microwave (75 W, 140° C.) for 3 min to afford compound 11.

Figure 8:
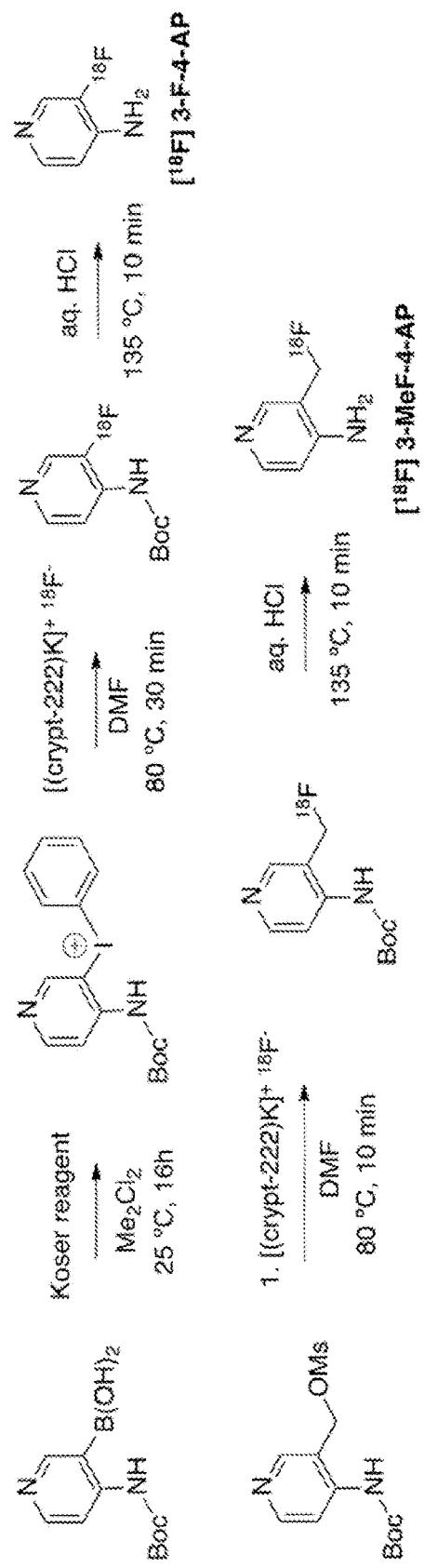
FIG. 8. Possible radiosynthesis of $[^{18}F]$ 3-F-4-AP and $[^{18}F]$ 3-MeF-4-AP FIGS. 9A-9B—(A) Experimental scheme: TBI is induced in rats using a controlled impact. (B) Autoradiography.

Alternatively, the $^{18}$F-labeled versions of 3-F-4-AP and 3-MeF-4-AP are synthesized as depicted below based on the synthesis of similar PET markers (FIG. 8) (Zhou, et al., 2009; Lee, et al., 1999; Dolle, et al., 2005; Cai, et al., 2008; Chun, et al., 2012).

The proposed synthesis of [$^{18}$F] 3-F-4-AP uses iodonium salts for high efficiency synthesis of aryl fluorides (Chun, et al., 2012). This tracer may be useful to evaluate lesion size and lesion load in multiple sclerosis patients. This tracer may also be useful in patients with Parkinson's disease, stroke, Cerebral palsy, Alzheimer disease, ALS, Lambert Eaton, brain tumors and other diseases.

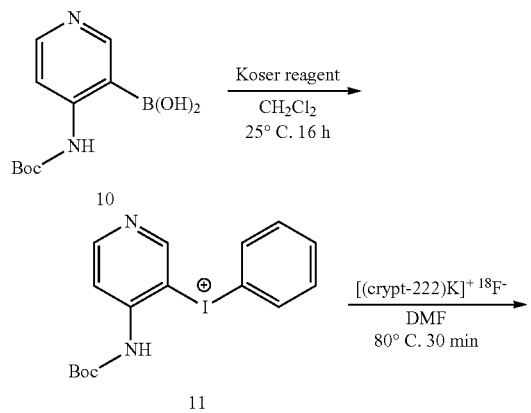

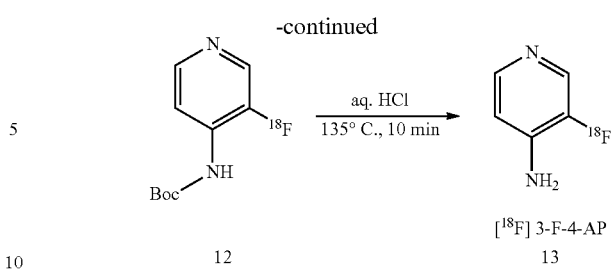

Synthesis of [$^{18}$F] 3-F-4-AP (13): Koser reagent is added to a solution of 4-[(tert-butoxycarbonyl)amino]pyridin-3-ylboronic acid (10) in CH$_2$Cl$_2$ and stirred until formation of {4-[(tert-butoxycarbonyl)amino]pyridin-3-yl}(phenyl)iodonium (11). After 16 h the solvent is removed under vacuo and the product (11) purified using standard techniques. Next {4-[(tert-butoxycarbonyl)amino]pyridin-3-yl}(phenyl) iodonium (11) is dissolved in DMF and [(crypt-222)K]$^+$ 18F$^-$ is added to generate [$^{18}$F] N-(3-fluoropyridin-4-yl) carbamate (12). Finally, [$^{18}$F] N-(3-fluoropyridin-4-yl)carbamate (12) is treated with aqueous HCl to deprotect the amino group and yield the final product [$^{18}$F] 3-fluoropyridin-4-amine also known as [$^{18}$F] 3-fluoro-4-aminopyridinine or [$^{18}$F] 3-F-4-AP Example 7 (Prophetic Example). Use of the Compounds for Imaging in Animal Models of Demyelination Once the radiolabeled markers are obtained, the inventors will perform imaging studies in several mouse models of demyelination. The compounds are tested for imaging demyelination as previously described (Stankoff et al., 2011). The use of different mouse models will enable the inventors to assess whether 4-AP mainly targets potassium channels in neurons or also channels in other cells such as lymphocytes. Suitable animal models, in particular, mouse models, are contemplated as follows.

DTA Model.

The inventors have generated a new mouse model (DTA) of widespread CNS demyelination wherein the ablation of oligodendrocytes is accomplished via cell-specific activation of diphtheria toxin (DT-A) expression in young adult animals (Traka et al., 2010). This approach results in widespread DT-A-mediated death of mature oligodendrocytes and extensive demyelination throughout the CNS (Traka et al., 2010). At the peak of disease the DTA mice developed severe tremor and ataxia. These mice demonstrate a gradual recovery that culminates in full attenuation of the disease symptoms by approximately 70 dpi, which correlates with the repopulation of oligodendrocytes and remyelination. This model provides widespread and extensive demyelination of the CNS.

Cuprizone-Induced Demyelination.

Feeding of cuprizone (bis-cyclohexanone oxaldihydrazone) to young adult mice induces a synchronous and consistent demyelination of the corpus callosum (Matsushima and Morel, 2001; Stidworthy et al., 2004). Demyelination and oligodendrocyte apoptosis do not involve T cells or breakdown of the blood-brain barrier in this model and the mice do not display any clinical symptoms. Following the loss of oligodendrocytes and demyelination, there is a repopulation of the oligodendrocytes in the corpus callosum and robust remyelination. The inventors have considerable experience using the cuprizone protocol to examine the demyelination and remyelination processes (Gao et al., 1999; Lin et al., 2004). The cuprizone model provides a nice system in which to image highly reproducible, focal demyelinated lesions that do not involve peripheral immune system infiltration.

Experimental Autoimmune Encephalomyelitis (EAE).

EAE which is considered the best animal model of MS, can be induced in a variety of species of laboratory animals by immunization with either myelin or one of its components (*Prog. Clin. Biol. Res.*, 1984; Zamvil and Steinman, 1990; Martin and McFarland, 1995). EAE is an immune-mediated demyelinating disease that displays many of the clinical, pathologic, and immunological features of MS (Behi et al., 2005). Clinical symptoms correlate with focal inflammatory demyelinated lesions in the spinal cord of the affected animals. The EAE model is capable of providing the most MS-like lesions, which include loss of oligodendrocytes, demyelination and T cell infiltration.

Other animal models of demyelination, such as a lysolecithin injection model, may also be used in the study of demyelination associated diseases. Animal models other than mouse models may also be used. It will be obvious to those skilled in the art to choose an appropriate animal model to adapt to intended research purposes.

Traumatic brain injury models. In these models a traumatic brain injury is caused in mice or rats by a controlled impact (using a pendulum or a weight) or by an explosion.

Example 8. (Prophetic Example) Use of the Compounds Described Herein for Diagnosis and Evaluation of MS Progression A detectable amount of the compound described herein, such as [$^{18}$F]-3-fluoromethyl-4-aminopyridine, or [$^{18}$F]-3-fluoro-4-aminopyridine, is introduced in the patient body via a pharmaceutically acceptable route known in the art. The patient is positioned inside a PET scanner or an instrument capable of detecting radiation emitted by the compound as typically done in the art. The localization of the radioactive tracer is done using a computer, which can provide images of the localization and extent of demyelinated axons.

Example 9. Methods

Non-Radioactive Synthesis:

Non-radioactive synthesis has been performed using standard techniques in organic chemistry. Reactions were monitored by TLC and products characterized by $^1$H, $^{13}$C and $^{19}$F NMR, and high-resolution mass spectroscopy.

All chemicals were ordered from Sigma unless otherwise specified. Animal protocols were approved by IACUC.

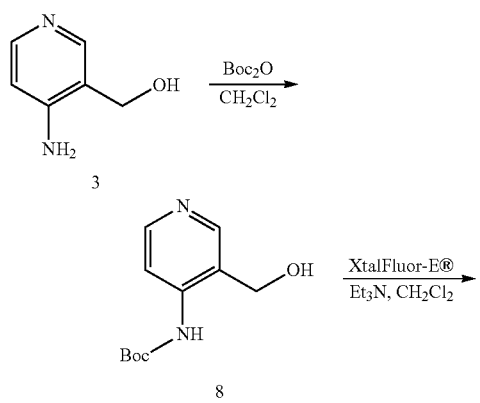

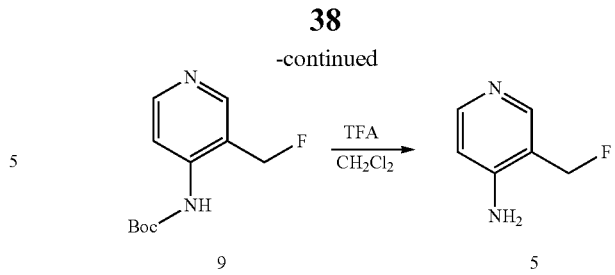

Synthesis of tert-butyl N-[3-(hydroxymethyl)pyridin-4-yl]carbamate (8)

To a solution of 4-aminopyridine-3-methanol (3) (Alfa Aesar) (806 mg, 6.5 mmol) in CH$_2$Cl$_2$ (10 mL) a solution of di-tert-butyl-dicarbonate (1.43 g, 6.56 mmol) in CH$_2$Cl$_2$ (5 mL) was added and stirred at room temperature for 1 h (TLC). After 1 h, the solution was acidified with 1 N HCl (7.4 mL, 7.4 mmol). The phases were separated and the aqueous phase was washed with CH$_2$Cl$_2$. The aqueous layer was mixed with a fresh portion of CH$_2$Cl$_2$ (10 mL) and treated with K$_2$CO$_3$ (711 mg, 5.1 mmol). The phases were separated and treated with additional amounts of CH$_2$Cl$_2$. The combined organic extracts were dried (MgSO$_4$) and evaporated in vacuo to give a 60:40 mixture containing desired product 8 and the O-linked carbonate. Attempts to purify the N-carbamate by flash chromatography from the O-carbonate were unsuccessful due interconversion between these two species in solution at room temperature. $^1$H-NMR (CDCl$_3$, 500 MHz) δ: 1.53 (9H, s), 4.67 (2H, s), 4.83 (2H, br s), 7.95 (1H, s), 8.07 (1H, d, J=5.5 Hz), 8.28 (1H, d, J=5.5 Hz), 8.48 (1H, s). This product has been previously synthesized through a different route (Mochizuki, et al., 2011).

Synthesis of tert-butyl N-[3-(fluoromethyl)pyridin-4-yl]carbamate (9)

To a solution of triethylamine (450 µL, 2.76 mmol) in CH$_2$Cl$_2$ (5 mL) at −78° C. was added XtalFluor-E® (473 mg, 207 mmol) and the product from the previous reaction (310 mg, 1.38 mmol in 5 mL CH$_2$Cl$_2$). The reaction was stirred at 0° C. for 15 min (TLC). Subsequently, the reaction mixture was washed with NaHCO$_3$ (10 mL) and brine (10 mL). The organic phase was dried (MgSO$_4$) and concentrated in vacuo. The crude product was purified by flash chromatography to afford 9 (113 mg, 36% yield). R$_f$=0.5 (1:1, hexanes: EtOAc). $^1$H-NMR (CDCl$_3$, 500 MHz) δ ppm: 1.56 (9H, s), 5.48 (2H, d, J=48 Hz), 7.12 (1H, br s), 8.12 (1H, d, J=5.5 Hz), 8.38 (1H, d, J=3 Hz), 8.32 (1H, s), 8.53 (1H, dd, J$_2$=5.5 Hz, J$_1$=1.0 Hz). $^{13}$C-NMR (CDCl$_3$, 125 MHz) δ: 28.2, 80.6, 82.0 (d, J=15.5 Hz), 113.2, 118.0 (d, J=15.5 Hz), 145.6, 150.1, 149.7, 151.7, 152.4. $^{19}$F-NMR (CDCl$_3$, 470 MHz) δ: −209.3 (t, J=48 Hz). HR-MS m/z: 227.1190 (M+H)$^+$.

Synthesis of 3-fluoromethyl-4-aminopyridine (5)

To a solution of 9 (56 mg, 0.25 mmol) in CH$_2$Cl$_2$ (3 mL) was added TFA (194 µL, 2.5 mmol) at 0° C. and stirred at room temperature for 5 h (TLC). After 5 h the reaction was quenched with excess NaOH (1 M). The solvent was evaporated to afford 8 quantitatively. R$_f$=0.2 (MeOH). $^1$H-NMR (500 MHz, D$_2$O) δ: 5.40 (2H, d, J=48 Hz), 6.87 (1H, d, J=7 Hz), 7.95 (1H, d, J=7 Hz), 8.09 (1H, s). $^{19}$F-NMR (CDCl$_3$, 470 MHz) δ: −215.9 (t, J=48 Hz). HR-MS m/z: 127.0666 (M+H)$^+$.

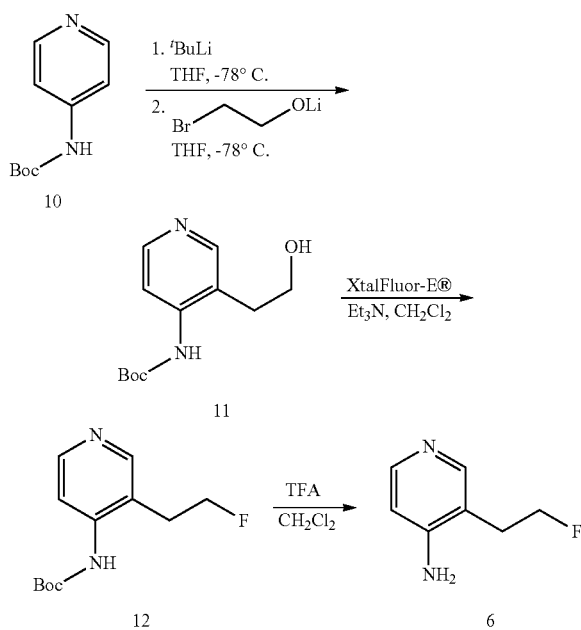

Synthesis of tert-butyl N-[3-(2-hydroxyethyl)pyridin-4-yl]carbamate (11)

Adapted from Spivey et al: To a solution of 4-(Boc-amino)pyridine (1) (2.0 g, 10.3 mmol, 1 eq.) in 25 mL of dry THF at −78° C. was added t-BuLi (14.5 mL, 1.7 M, 24.7 mmol, 2.4 eq.) in pentane over 30 min. The resulting bright yellow suspension was stirred at −78° C. for 15 min, at −15° C. for 2 h and then recooled to −78° C. In a separate flask, n-BuLi (7.38 mL, 2.5M, 18.54 mmol, 1.8 eq) in hexanes was added to a solution of 2-bromoethanol (1.294 mL, 15.45 mmol, 1.5 eq) in 20 mL of dry THF at −78° C. and stirred for 10 min. After 10 min, the bromoethanol solution was transferred via cannula to the flask containing lithiated N-boc-4-aminopyridine over 10 min. The reaction was allowed to warm to room temperature and the mixture was stirred for 2 h. The reaction was recooled to −78° C. and quenched with 5 mL of water. The solution was partitioned between water (20 mL) and $CH_2Cl_2$ (30 mL). The phases were separated and the extraction was completed with additional portions of $CH_2Cl_2$. The combined organic extracts were washed with brine, dried over $MgSO_4$ and evaporated under vacuum. The crude product was dissolved in a small amount of $CH_2Cl_2$ purified by silica gel chromatography (EtOAc) to afford the product 11 (0.678 g, 36% yield). $R_f$=0.15 (EtOAc). $^1$H-NMR (500 MHz, $CDCl_3$) δ: 1.51 (9H, s), 2.81 (2H, t, J=5.0 Hz), 3.80 (1H, br s), 3.94 (2H, t, J=5.0 Hz), 7.92 (1H, d, J=5.5 Hz), 8.15 (1H, s), 8.27 (1H, d, J=5.5 Hz), 8.63 (1H, s).

Synthesis of tert-butyl N-[3-(2-fluoroethyl)pyridin-4-yl]carbamate (12)

To a solution of $Et_3N$-3HF (715 μL, 4.39 mmol, 2 eq.) in 5 mL of dry $CH_2Cl_2$ at 0° C., XtalFluor (753 mg, 3.29 mmol, 1.5 eq) was added and stirred for 5 min. After 5 min, 2 (525 mg, 2.195 mmol, 1 eq) was added and the reaction was monitored by TLC (1:1, hexanes:EtOAc). 15 min later the reaction was washed with $NaHCO_3$ (5 mL) and brine (5 mL), dried with $MgSO_4$ and the solvent evaporated under vacuum. The crude product was dissolved in a small amount of $CH_2Cl_2$ and purified by silica gel chromatography to afford 3 (457 mg, 71% yield). $R_f$=0.4 (1:1, hexanes:EtOAc). Mp=103° C. $^1$H-NMR (500 MHz, $CDCl_3$) δ: 1.53 (9H, s), 2.98 (2H, dt, $J_2$=29 Hz, $J_1$=5.8 Hz), 4.72 (2H, dt, $J_2$=47 Hz, $J_1$=5.8 Hz,), 7.04 (1H, d, J=7.5 Hz), 7.99 (1H, d, J=5.0 Hz), 8.32 (1H, s), 8.40 (1H, d, J=5.0 Hz). $^{13}$C-NMR ($CDCl_3$, 125 MHz) δ: 28.2, 30.4 (d, J=20.1 Hz), 81.6, 84.9 (d, J=165 Hz), 113.7, 121.0, 144.7, 149.7, 151.2. $^{19}$F-NMR ($CDCl_3$, 470 MHz) δ: −213.3 (tt, $J_2$=47 Hz, $J_1$=29 Hz). HR-MS m/z: 241.1347 (M+H)$^+$.

Synthesis of 3-fluoroethyl-4-aminopyridine (6)

To a solution of 12 (120 mg, 0.5 mmol, 1 eq.) in 5 mL of $CH_2Cl_2$ was added TFA (191 μL, 2.5 mmol, 5 eq) at 0° C. The reaction was allowed to warm up to room temperature and stirred for 5 h (TLC). After 5 h, the reaction was quenched with excess NaOH (1 M) and extracted multiple times with $CH_2Cl_2$. The solvent was evaporated to afford 4 quantitatively. $R_f$=0.5 (MeOH). $^1$H-NMR (500 MHz, $CDCl_3$) δ: 2.91 (2H, dt, $J_2$=26.5 Hz, $J_1$=6 Hz), 4.26 (2H, br s), 4.69 (2H, dt, $J_2$=47 Hz, $J_1$=6 Hz), 6.54 (1H, d, J=5.5 Hz), 8.13 (1H, s), 8.15 (1H, d, J=5.5 Hz). $^{13}$C-NMR ($CDCl_3$, 125 MHz) δ: 30.2 (d, J=20.6 Hz), 84.2 (d, J=166 Hz), 110.1, 149.1, 151.0, 151.7. $^{19}$F-NMR ($CDCl_3$, 470 MHz) −213.3 (tt, $J_2$=47 Hz, $J_1$=26.5 Hz). HR-MS m/z: 141.0823 (M+H)$^+$.

[$^{18}$F] Labeling (Prophetic):

$^{18}$F-labeling will be performed using cyclotron-generated reagents for nucleophilic and electrophilic fluorination.

Measure Compound Action Potential of Demyelinated Nerves:

4-AP can enhance the Compound Action Potential in demyelinated nerves. The effects of the 4-AP derivatives in the compound action potential of optic nerves and/or spinal cords from demyelinated animals will be measured according the protocol by Stys et al. Briefly, optic nerves will be removed postmortem and placed in an oxygenated aCSF solution. Suction electrodes will be used to measure CAP in the presence and absence of the test compounds (Stys et al., 1991).

Imaging (Prophetic):

Six mice of each group (DT-A, Cuprizone, EAE and healthy controls) will be used for the Imaging study. 100 μCi/100 μL of [$^{18}$F]-labeled 4-AP derivative will be injected into the tail vein of anesthesized mice. The imaging sessions will be carried out as 1 h dynamic scan using the MicroPET scanner. The MicroPET data will be processed using filter back projection algorithm with attenuation and scatter corrections. In vitro stability studies of the radioactive tracers will be performed according to the protocol by Zhou et al. (2009). Briefly, 2 mL of heparinized mouse blood (C57BL/6N mice) are incubated with the radioactive tracer (~400 μCi) for 5 min, 30 min, 1 h and 2 h at 37° C. At each time point the blood will be lysed with 3 volumes of ethanol and centrifuged. The radioactive species in the supernatant will be analyzed by radio-TLC and compared to the radioactive tracer's control. In vivo stability: ~400 μCi of [$^{18}$F] 4-AP in 200 μL of saline are injected into a mouse by iv injection in the tail vein of an immobilized mouse. Blood samples (0.5 mL) are obtained via cardiac puncture under anesthesia at 5 and 30 min post-injection. Afterwards, the plasma is treated with 3 equivalents of acetonitrile and the pellet separated by centrifugation. The radioactive species of the supernatant will be analyzed by radio-TLC and compared to control. In vivo biodistribution time-course study: ~400 μCi of [$^{18}$F] 4-AP in 200 μL of saline will be injected into a mouse by iv injection. At 5 min, 30 min, 1 h and 2 h post injection the mice will be sacrificed and blood tissues and organs removed, weighed and counted using a Beckman counter with standard diluted aliquots of the sample. The percent injected dose per gram of tissue will be calculated.

Neurological Evaluation (Prophetic):

the effects of the 4-AP derivatives in demyelinated animals will be evaluated using a rotorod to test for balance and coordination, the inventors will also measure changes in tremor and other functions.

Pharmacology of 4-AP Derivatives (Prophetic):

metabolic stability, membrane permeability, toxicity, pharmacokinetic and drug distribution studies will be conducted with the assistance of a third party research contract organization.

Measurement of 4-AP and Derivatives Distribution in Mice (Prophetic):

The distribution of 4-AP and derivatives will be measured using MALDI-IMS, whole body autoradiography, or organ autoradiography.

Example 10. Blockage of K$^+$ Channels by 4-AP Derivatives Using Voltage Clamp

The inventors tested the ability of compounds 1-7 to block voltage-gated K$^+$ channels expressed in *Xenopus* oocytes using the cut-open voltage clamp technique described by Stefani and Bezanilla. For this experiment, Shaker K$^+$ channel from *D. megalonaster* was chosen as the archetypical voltage gated K$^+$ channel that gives name to the family. Shaker shares an identity ranging from 69%-79% with neuronal K$_v$1.1, K$_v$1.2, K$_v$1.3, K$_v$1.4, K$_v$1.6 that are among the presumed targets of 4-AP and its sensitivity to 4-AP is comparable to other K$_v$1 channels (Gutman, et al., 2005; McCormack, et al., 1994). In order to compare the relative potency of the different 4-AP derivatives, each drug was applied at increasing concentrations and the ratio between the K+ current with and without drug was computed (FIG. 5).

Electrophysiology:

Electrophysiology studies are conducted according to the protocol by Stefani and Bezanilla (1998). Briefly, K$^+$ channel Shaker cRNA is injected into *Xenopus* oocytes 24 h after their surgical extraction from adult frogs. 1-5 days after injection channel currents are recorded using the cut-open voltage-clamp. Each molecule is added to the external solution at a range of concentrations and K+ currents recorded and compared to those with 4-AP.

Expression of Shaker K+ Channel in *Xenopus laevis* Oocytes:

K$^+$ channel expression in *Xenopus* oocytes membranes was achieved by injecting approximately 50 ng of WT Shaker cRNA (kit Ambion) into the oocytes 24 h after surgical extraction from adult frogs and collagenase treatment. Injected oocytes were maintained in a standard oocytes solution (100 mM NaCl, 5 mM KCl, 2 mM CaCl$_2$, and 10 mM Hepes at pH 7.5) at 16.5° C. and recordings were performed 1-3 days after injection.

Recording of K$^+$ Currents in *Xenopus* Oocytes:

K$^+$ currents were recorded from oocytes expressing Shaker K$^+$ channels using the cut-open voltage clamp technique as described by Stefani and Bezanilla. The internal solution was 120 mM KOH, 20 mM HEPES-methyl sulfonate (MES) pH 7.4, 2 mM EGTA. The external solution was 12 mM KOH, 105 mM N-methyl-D-glucamine-MES pH 7.4, 20 mM HEPES, 2 mM CaOH. To assess the effects of the 4-AP derivatives, the drug under study was added in incremental concentrations by exchanging the external solution (top and guard chambers) several times. After application, cells were voltage-clamped at least 5 min at 0 mV, then voltage-clamped at −80 mV for 1-2 min. K$^+$ currents were generated by applying series of 50 ms pulses from −70 mV to +40 mV in increments of 10 mV. The effect of the drug was assessed by measuring the relative intensity of the K$^+$ current before and after applying varying drug concentration at a constant voltage (typically +20 mV) and at the end of the test-pulse. Analysis of the traces was done using an in-house software. The half-maximal inhibitory concentration (IC$_{50}$) for each drug was calculated by plotting the relative K$^+$ current vs. concentration and fitted to the Hill equation using the software Origin.

In this experiment, it was demonstrated that 4-AP and 3-F-4AP are the most potent compounds with half-maximal inhibitory concentrations (IC$_{50}$) around 0.27 mM (4-AP: IC$_{50}$=0.29 mM, 95% C.I.=0.21-0.41 mM; 3-F-4-AP: IC$_{50}$=0.25 mM, 95% C.I.=0.13-0.44 mM), which is similar to what has been reported for other Shaker-like channels (Gutman, et al., 2005). Although Berger et al described 3-F-4-AP as being less potent than 4-AP in eliciting muscle twitches in dissected mouse hemidiaphragms, it was found to have comparable potency in blocking Shaker K$^+$ channel. In this assay, 3-MeOH-4-AP and 3-MeF-4-AP were found to be between 15 and 25 times less potent than 4-AP (3-MeOH-4-AP: IC$_{50}$=4.38 mM, 95% C.I.=3.4-5.6 mM; 3-MeF-4-AP: IC$_{50}$=7.45 mM, 95% C.I.=6.2-9.0 mM). In contrast, 3-EtF-4-AP and 2-F-4-AP have IC$_{50}$ values greater than 10 mM (95% C.I. not determined). These results demonstrate that only small modifications in the 2 position of 4-AP are permitted (e.g. 3-F-4-AP, 3-MeF-4-AP, 3-MeOH-4-AP) whereas larger modifications such as 3-EtF-4-AP or substitution in the 2 position such as 2-F-4-AP significantly diminish activity. In this experiment, it was also observed that these drugs are difficult to wash, out which is similar to what has been reported for 4-AP (McCormack, et al., 1994), suggesting a similar mode of binding.

Example 11. Effects of 4-AP Derivatives on the Compound Action Potential of Dissected Optic Nerve It is known that 4-AP can significantly enhance action potential of demyelinated fibers (Sherratt, et al., 1980; Devaux, et al., 2002). In order to determine if the drugs could also be effective in enhancing compound action potentials (CAP), the effects of these compounds on the CAP of hypomyelinated optic nerves from Shiverer mice (shi$^{-/-}$) and control mice (shi$^{+/-}$, shi$^{+/+}$) were tested. Shiverer mice lack compact myelin in the CNS due to a null mutation of the myelin basic protein gene (MBP). The results of this experiment are shown in FIG. 5.

Dissection of Optic Nerves from Shiverer Mice:

optic nerves were dissected from 12-16 week old Shiverer (shi$^{-/-}$) and control mice (shi$^{+/-}$ and shi$^{+/+}$). Mice were euthanized by CO$_2$ overdose and the optic nerves were quickly dissected between the eyeball and the optic chiasm. The nerves were incubated for 30 min at 37° C. in oxygenated (95% O$_2$, 5% CO$_2$) aCSF solution (126 mM NaCl, 3 mM KCl, 2 mM MgSO$_4$, 26 mM NaHCO$_3$, 2 mMCaCl$_2$, 10 mM dextrose, pH 7.5) before the experiment.

Optic Nerve Electrophysiology:

compound action potentials (CAP) from hypomyelinated nerves (Shiverer mice, shi$^{-/-}$) and myelinated nerves (litermate controls, shi$^{+/-}$ and shi$^{+/+}$) were recorded using suction electrodes as described by Stys et al. Briefly, the dissected optic nerve was placed inside a chamber containing oxygenated (5% $CO_2$, 95% $O_2$) aCSF (300 µL) between two suction electrodes (stimulus and recording electrodes) forming a tight seal on each end. Two additional electrodes were placed in the bath for reference. A supramaximal pulse (250 mV, 20 µs) was applied at the stimulating end of the nerve. The resulting CAP was amplified from the recording electrode using a high impedance low-noise amplifier (EG&G Princeton Applied Research Corporation) and filtered and sampled at 10-100 kHz. To assess the effects of the 4-AP derivatives on the CAP, the drug under study was added in incremental concentrations to the recording chamber after the CAP was allowed to stabilize for 5 min while pulsing repeatedly. After each measurement the chamber was washed for 5 min (flow 1 mL/min) with oxygenated aCSF. The study was conducted at 22.2±1.3° C. to allow for slower conduction and the temperature was monitored throughout the experiment. CAP recordings were acquired with a SBC6711 board (Innovative Integration) controlled by in-house written software. Analysis of the traces was done using an in-house software. The half-maximal effective concentration ($EC_{50}$) for each drug was calculated by plotting the final over initial amplitude vs. concentration and fitted to the Hill equation using Origin.

Figures 4A, 4B, 4C:
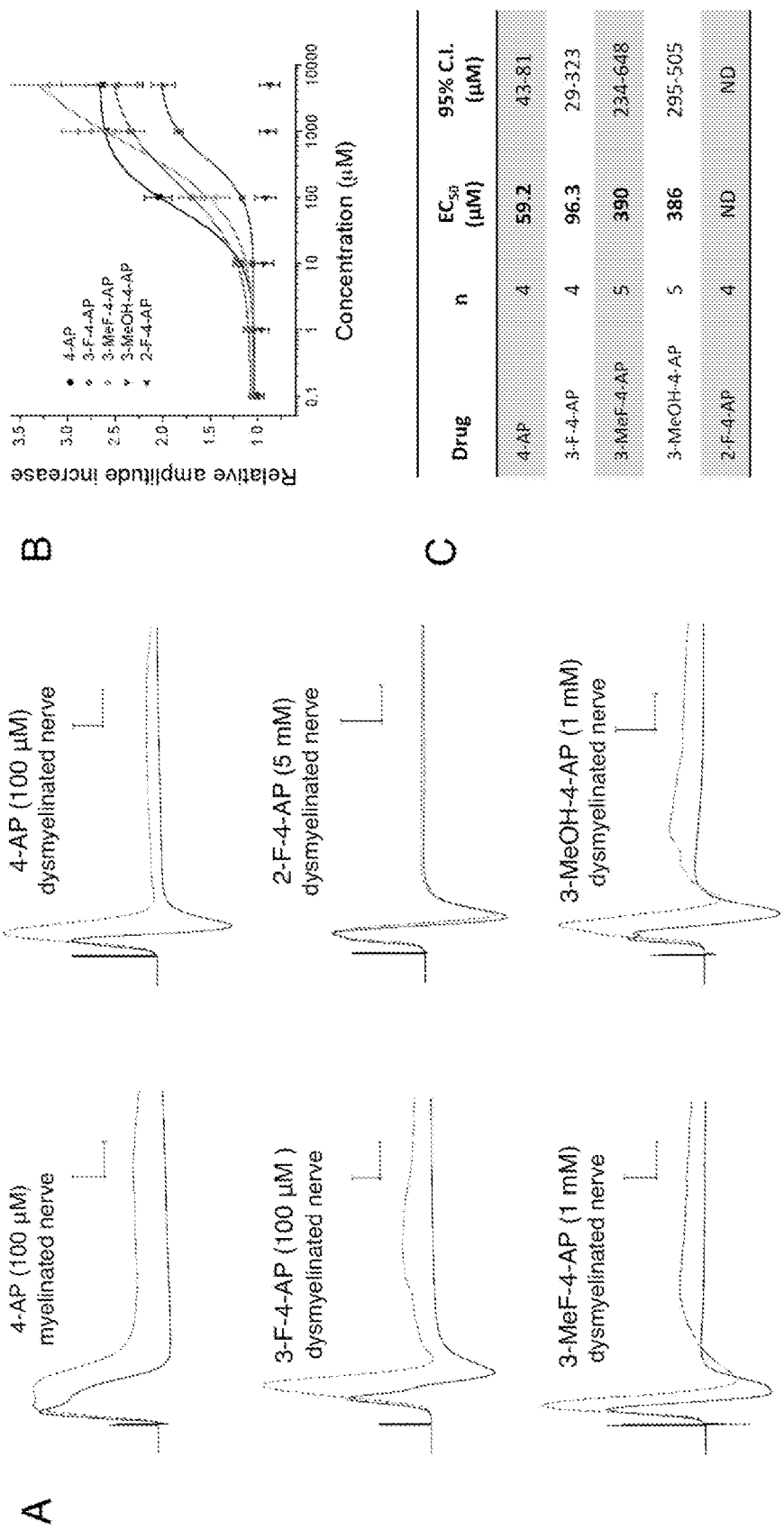
FIGS. 4A-4C show enhancement of compound action potential (CAP) by 4-AP derivatives. (A) CAP traces before (solid line) and after (dashed line) addition of the drug. Scale bar: 5 mV/5 ms. (B) Relative increase of maximum CAP amplitude vs. concentration for each drug. Amplitude was normalized to the amplitude before the drug. (C) Half-maximal effective concentration of each molecule and 95% confidence interval obtained from fitting the data to the Hill equation. n=number of times each drug was tested.

This experiment shows the typical differences between normally myelinated nerves and hypomyelinated nerves. The Shiverer's hypomyelinated nerves conducted much slower (average conduction velocity 0.59±0.10 m/s vs. 1.4±0.3 m/s at 22° C.), had a smaller CAP amplitude (20-30% compared to myelinated nerves) and showed a larger undershoot than control nerves. Addition of 4-AP to normally myelinated nerves caused small increases in CAP amplitude of around 5% and broadening of the signal, whereas addition of 4-AP to hypomyelinated nerves caused large increases in CAP amplitude of 2-4 fold generating a CAP that, although delayed, almost looked like a normally myelinated nerve (FIG. 4A). As for the effect of the different derivatives, 4-AP and 3-F-4-AP were found to be the most potent in enhancing the CAP with half-maximal effective concentrations ($EC_{50}$) of 59.2 µM (95% C.I. 43-81 µM) and 96 µM (95% C.I. 29-323 µM) respectively. The derivatives 3-MeOH-4-AP and 3-MeF-4AP were around 4-6 times less potent with $EC_{50}$'s around 390 µM (3-MeOH-4-AP: $IC_{50}$=386 µM, 95% C.I.=295-505 µM; 3-MeF-4-AP: $IC_{50}$=286 µM, 95% C.I.=234-648 µM). As expected, 2-F-4AP had no effect demonstrating that the observed effects with the other derivatives are specific. 3-EtF-4-AP was not included in this experiment since it was already found to be inactive by voltage clamp. The trend observed in this experiment was consistent with what was observed in the voltage-clamp experiment indicating that the increase in CAP is due to blockage of voltage-gated $K^+$ channels. Interestingly, the $EC_{50}$ values calculated from this experiment were significantly lower than what was measured using voltage-clamp.

Example 12. Pharmacology of 3-F-4-AP and 4-AP

The permeability of 3-F-4-AP and 4-AP to an artificial membrane made of porcine brain polar lipids was tested. In this experiment, the inventors included highly permeable verapamil and lowly permeable theophylline as controls. The inventors found 3-F-4-AP to be 6.6-times more permeable than 4-AP ($P_e$: 15.6±0.6 nm/s vs. 2.36±0.03 nm/s, FIG. 6A). This value correlates well with the predicted partition coefficients in octanol/water for these drugs (c Log P: 0.26 vs. 0.03, Pearson r=0.997, P value=0.0033).

Figures 6A, 6B:
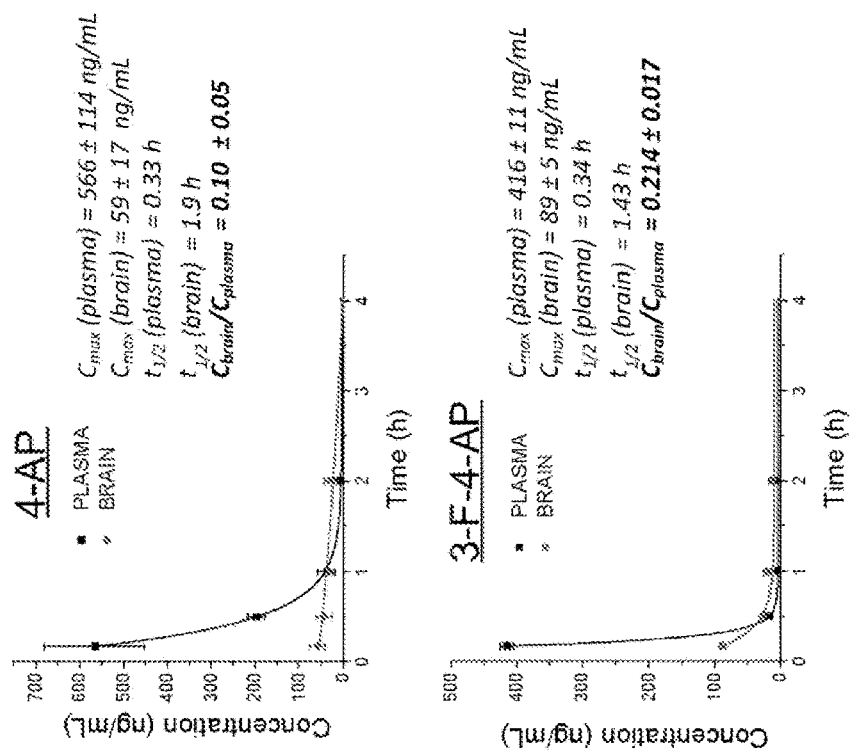
FIGS. 6A-6B show pharmacology of 4-AP derivatives. (A) Pharmacological parameters for 4-AP derivatives and control compounds. c Log P: calculated partition coefficient using VCCLAB (I. V. Tetko et al., Virtual computational chemistry laboratory—design and description. *Journal of computer-aided molecular design* 19, 453 (June, 2005)), $P_e$: permeability coefficient across artificial membrane (n=3), $t_{1/2}$: half-life in mouse microsomes (n=3). (B) Pharmacokinetic profile of 4-AP and 3-F-4-AP in plasma and brain of mice after intravenous injection of 0.75 mg of drug per mouse kg (n=3 mice per time point).

The stability of these drugs in mouse plasma and mouse liver microsomes was also tested. Liver microsomes contain large amounts of cytochrome P450 and can be used to estimate the metabolic stability of drugs. In this experiment, highly stable verapamil and lowly stable propanolol were included as controls. Both drugs were found to be stable in plasma (>93% remaining after 1 h) and 3-F-4-AP was found to be 2.7-times more stable than 4-AP in microsomes (4-AP: $t_{1/2}$=53±10 min; 3-F-4-AP: $t_{1/2}$=144±11 min) (FIG. 6A).

Pharmacokinetic profiling of 4-AP and 3-F-4-AP in mice after a single intravenous dose of the drugs at 0.75 mg/kg (FIG. 6B) was also performed. In this experiment, it was found that 4-AP and 3-F-4-AP have a short half-life in plasma (0.33 h and 0.34 h, respectively) and a moderate half-life in brain (1.9 h and 1.43 h, respectively). Interestingly, it was observed that 3-F-4-AP reaches a significantly higher concentration in the brain indicated by the ratio between the maximum dose in the brain over the maximum dose in plasma ($C_{brain}/C_{plasma}$: 0.214±0.17 vs. 0.10±0.05). This result is consistent with the previous experiment which showed that 3-F-4-AP can diffuse faster across hydrophobic membranes. Taken together these experiments demonstrate that 3-F-4-AP has better stability and better brain permeability than 4-AP.

In Vivo Effects:

10-week-old female C57Bl/6J mice were given an intraperitoneal injection of the drug under investigation and monitored continuously for 4 h. After 4 h no signs of drug effects could be observed. At least 72 h passed between injections to the same mice.

Parallel Artificial Membrane Permeability Assay (PAMPA):

Permeability studies were performed as previously described by Sugano, et al., 2011. A 96-well microplate (acceptor compartment) was filled with PBS containing 5% DMSO. A hydrophobic filter plate (donor compartment) was placed atop the buffer-filled plate and the filter surface was impregnated with 5 µL solution of porcine polar brain lipids (Avanti Lipids) in dodecane (1% w/v). 150 µL of the test compounds dissolved in PBS containing 5% DMSO (compound concentration 0.5 mM) was added to the donor compartment and covered. The only barrier between the two compartments was the artificial BBB membrane containing the porcine polar brain lipids. The whole system was incubated for several hours. Time of incubation was chosen considering c Log P of tested compounds (4 h for Verapamil and 16 h for 4-aminopyridine, 3-fluoro-4-aminopyridine and theophylline). Samples from the acceptor compartment were analyzed by UV-VIS spectrophotometry (4-aminopyridine: 260 nm, 3-fluoro-4-aminopyridine: 265 nm) and compared to reference solutions.

Stability in Plasma:

Plasma stability was conducted by incubating each compound at initial concentration of 1 µM in mouse plasma for 60 minutes. Samples were collected at 0, 20, 40 and 60 minutes and the reaction was stopped by addition of 1 vol. of acetonitrile. The loss of compound was determined using LC-MS comparing the peak area at several time points. Half-life time was calculated from linear regression of time course data.

Stability in Microsomes:

study compounds were incubated at initial concentration of 1 µM with liver microsomes from CD1 mouse (0.04 mg/mL) in PBS in the presence or absence of enzyme cofactors (1.3 mM $NADP^+$, 3.3 mM $MgCl_2$, 3.3 mM G6P and 1 U/ml G6PDH, 1 mM UDPGA and 4.7 µg/ml Alamethicin). After t=0, 20, 40 and 60 min, a sample was removed and the reaction was stopped by adding 1 volume of acetonitrile. The loss of compound was determined by LC-MS analysis comparing the amount of compound in the sample to the respective reference samples (without cofactors). To ensure that the assay is reliable, Propanolol and Verapamil were included as control compounds. The results were normalized for reaction volume and protein concentration.

LC-MS:

The following conditions were used for LC-MS analysis. Solvent A: Water (0.1% Formic acid). Solvent B: Acetonitrile (0.1% Formic acid). Flow rate: 0.5 ml/min. Gradient conditions: 0.0-0.5 min 95% B, 0.5-6.0 min 5% B, 6.0-6.5 min 5% B, 6.5-6.6 min 95% B, 6.6-7.5 min 95% B. Running time: 7.5 min. Injection volume: 40 µl. Column: Luna HILIC, 150×4.6 mm, 3 µm. Ionization mode: ESI positive. MS mode: Multiple Reaction Monitoring (MRM). Capillary voltage: 4500 V. Nebuliser gas: 40 psi. Dry gas: 9 L/min. Dry Temperature: 300° C. HPLC and MS/MS parameters: 4-aminopyridine retention time 3.5 min, ion product 94.9. 3-fluoro-4-aminopyridine retention time 4.0 min, ion product=112.9.

Pharmacokinetic Study:

39 mice (CD-1, 6-weeks old, female) were used in the study. 18 mice were administered 4-aminopyridine, 18 mice were administered 3-fluoro-4-aminopyridine and 3 were left untreated. The drugs were dissolved in PBS and administered via tail-vein injection to achieve a dose of 0.75 mg/kg of body weight. At specific times post injection (10 min, 30 min, 1 h, 2 h, 4 h and 24 h) blood and brain samples were collected. Blood samples were transferred into tubes containing 5% EDTA, stored on ice, and centrifuged (4° C., 1000 rpm, 15 min). Plasma (upper phase) was transferred to a new tube and stored at −80° C. for further analysis. Brain tissue samples were collected after intracardial perfusion of the mouse. Brain tissue samples were stored at −80° C. for further analysis. Drug quantification in plasma: Briefly, to a 1.5 mL Eppendorf tube containing 50 µl of plasma, 200 µl of ice-cold acetonitrile containing 1,000 ng/ml Progesterone (used as internal standard) was added in order to precipitate the proteins. The sample was vortexed, mixed and centrifuged at 4000×g for 10 min at 4° C. to remove precipitates. 140 µl supernatant was collected and transferred to a 500 µl 96-well polypropylene plate and covered using silicone plate mat. 40 µl of sample was injected in into LC-MS. Using the same sample preparation procedure 11 standard solutions ranging from 50 ng/mL to 100 µg/mL were prepared, analyzed by LC-MS and used as a calibration curve to correlate peak area of the samples to concentration. Drug quantification in brain: the mouse brain was weighted and 1 mL of water per 400 mg of tissue was added. The sample was homogenized using an electric tissue homogenizer. To a 1.5 mL Eppendorf tube containing 50 µl of homogenized sample, 200 µl of ice-cold acetonitrile containing 1000 ng/ml Demeclocycline (used as internal standard) was added in order to precipitate the proteins. The sample was vortexed, mixed and centrifuged at 4000×g for 10 min at 4° C. to remove precipitates. 140 µl supernatant was collected and transferred to a 500 µl 96-well polypropylene plate and covered using silicone plate mat. 40 µl of each sample was injected into LC-MS. Using the same sample preparation procedure 11 standard solutions ranging from 50 ng/mL to 100 µg/mL were prepared, analyzed by LC-MS and used as a calibration curve to correlate peak area of the samples to concentration.

Data Analysis:

The Hill equation used to fit the data from the voltage-clamp and the optic nerve experiments was as follows: $y=y_0+(y_f-y_0)*x^n/(k^n+x^n)$; where n refers to the Hill coefficient (typically 1±0.1) and k refers to $EC_{50}$ or $IC_{50}$. $y_0$ and $y_f$ refers to the origin and final ordinate values and were fixed at 1±0.1 or 0±0.1 depending on the experiment. $EC_{50}=10^{<log\ EC50>}$; where $<log\ EC_{50}>$=average of log $EC_{50}$ values from all experiments with the same drug. 95% C.I.=[Upper Limit . . . Lower Limit]; where $U.L.=10^{(log\ EC50+s.d.)}$ and $L.L.=10^{(log\ EC50-s.d.)}$. The half-life ($t_{1/2}$) in the stability and pharmacokinetic experiments was calculated by fitting the data to the equation $C_t=C_0*exp(-k*t)$ where $C_0$=initial concentration, $C_t$=concentration at time t, and $k=ln\ 2/t_{1/2}$. Student t-test was used to compare results and $P<0.05$ was considered significant.

Example 13. Evaluation 4-AP Distribution in Partially Demyelinated Brains Using Autoradiography The inventors conducted an experiment to evaluate if 4-AP selectively localizes in demyelinated (injured) areas. In this experiment, tritium labeled 4-aminopyridine ([$^3$H] 4-AP) was injected into mice containing demyelinating lesions in the brain. The lesions were caused by prior injection of lysophosphatidylcholine (LPC), also called lysolecithin, into their brains, which causes focal demyelination at the site of injection. Two days after LPC injection, at the peak of demyelination, the animals were injected with [$^3$H] 4-AP (0.4 µCi/g) via tail vein injection. Twenty to sixty minutes after injection of [$^3$H] 4-AP the mice were euthanized and their brains were dissected and frozen. The frozen brains were then cut into 20 µm sections using a cryostat and the sections mounted in slides. The slides were then exposed to radiation sensitive X-ray film at −80° C. in the dark for forty days to capture the distribution of radioactivity coming from [$^3$H] 4-AP throughout the brain.

After autoradiographic exposure, the slides were stained for myelin basic protein (MBP) using immunohistochemistry and imaged using fluorescent microscopy to determine the areas of demyelination. The results of this experiment are shown in FIGS. 7A-E.

Figures 7A, 7B, 7C, 7D, 7E:
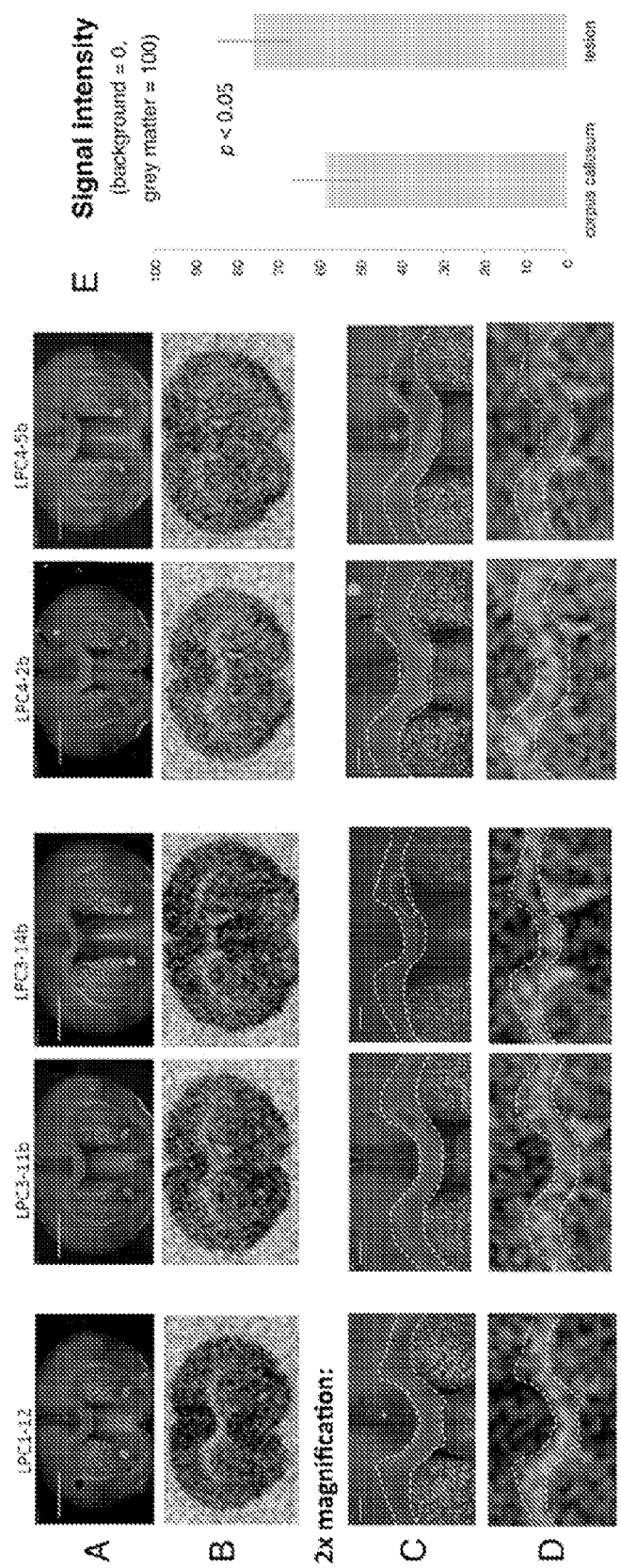
FIGS. 7A-7E. Brain distribution of 4-AP in mice injected with LPC. Top label represents mouse name+section number. (A) Fluorescent microscopy of myelin basic protein (MBP) immunostaining. Each small square represents one picture at 40×. Areas rich in MBP appear darker. Partial demyelination is evident in certain areas of the corpus callosum. (B) Autoradiography: areas where 4-AP localizes appear darker. 4-AP mostly localizes in grey matter areas with almost no signal in white mater areas. (C and D) 2× magnification of the corpus callosum area from A and B. Areas of demyelination in the corpus callosum appear darker than the rest of the corpus callosum. The corpus callosum has been marked with a dashed white line and the areas of demyelination within the corpus callosum have been circled with a solid white line. Autoradiographic signal is more intense in areas of demyelination compared to the rest of the corpus callosum. Scale bar=2 um. All animals pictured here received LPC injections however not all of them showed lesions at the level of sectioning (ie. no lesions are observed in LPC1-12). (E) Quantification of the mean pixel intensity in the whole corpus callosum and in the lesion area (as determined by IHC).

In this experiment, partial demyelination in distinct areas on the right side of the corpus callosum where lysolecithin was injected (FIG. 7C, circled in red) were seen. In those areas, the autoradiographic signal appears darker than the rest of the corpus callosum (FIG. 7D). The inventors quantified the signal in those areas and observed a statistically significant increase in signal in demyelinated areas (FIG. 7E).

This experiment demonstrates that 4-AP selectively localizes to grey matter areas and there's virtually no 4-AP in white matter areas. It was also observed that demyelination of white matter areas causes a local increase in the autoradiographic signal indicating that 4-AP localizes to demyelinated areas but not myelinated areas. The conclusion is that 4-AP does not bind to white matter areas unless there is demyelination.

It was shown that fluorinated 4-APs can block Shaker $K^+$ channel similar to 4-AP, that fluorinated 4-APs can enhance compound action potential of dysmyelinated optic nerves but have very little effect on normally myelinated optic nerves, and that fluorinated 4-APs have very similar in vivo effects as 4-AP. It was also shown that fluorinated 4-APs have enhanced permeability to the CNS relative to 4-AP. As 4-AP localizes to demyelinated areas and fluorinated 4-APs have very similar biological activity to 4-AP, it can be inferred that fluorinated 4-APs also localizes to demyelinated lesions. As fluorinated molecules can be used as PET tracers simply by exchanging the natural isotope of fluorine ($^{19}$F) for the positron emitting isotope $^{18}$F and this exchange does not alter the biological properties of the molecule, the evidence supports an inference that $^{18}$F-labeled 4-APs can serve as PET tracers for demyelination.

Example 14 (Prophetic). Distribution of [$^{14}$C] 3-F-4-AP in Partially Demyelinated Rat Brain and Spinal Cord Containing Demyelinated Lesions Using Autoradiography Rats will be injected with LPC in the brain and spinal cord to create focal demyelinated areas at the sites of injection. 1-6 days after LPC injection, the rats will be injected intravenously with [$^{14}$C] 3-F-4-AP (0.5 mg/kg, 0.5 uCi/g). 20-90 min after [$^{14}$C] 3-F-4-AP injection, the rats will be euthanized and their brains removed. Thin sections of the brain will be prepared using a cryostat and mounted into glass slides. The slides will be then exposed to a radiation sensitive film for up to 6 weeks. After exposure, the film will be developed and the slides will be processed for IHC. The distribution of the drug on the brain revealed by autoradiographic signal and compared with the distribution of myelin revealed by IHC. In some experiments, other $^{14}$C labeled fluorinated derivatives of 4-AP are used. In some experiments, $^{3}$H labeled fluorinated derivatives of 4-AP are used. In some embodiments, different rodent models of demyelination are used. In some embodiments, different species may be used.

Example 15 (Prophetic). Distribution of [$^{18}$F] 3-F-4-AP in Partially Demyelinated Rat Brain and Spinal Cord Using Pet Scanner The inventors will inject 0.005-50 mCi of [$^{18}$F] 3-F-4-AP or other $^{18}$F-labeled 4-AP derivative into LPC treated rats. Immediately after injection of the tracer, dynamic emission scan will be performed in 3D acquisition mode on the animal using a GMI microPET/SPECT/CT system. In order to quantify the images, the signal will be integrated in the lesion and compare it to the signal in the same area in a control animal. The results will be analyzed using statistical tests. In some experiments, other $^{11}$C labeled fluorinated derivatives of 4-AP are used. In some embodiments, different rodent models of demyelination are used. In some embodiments, different species may be used. In some embodiments, the species will be humans.

Figures 9A, 9B:
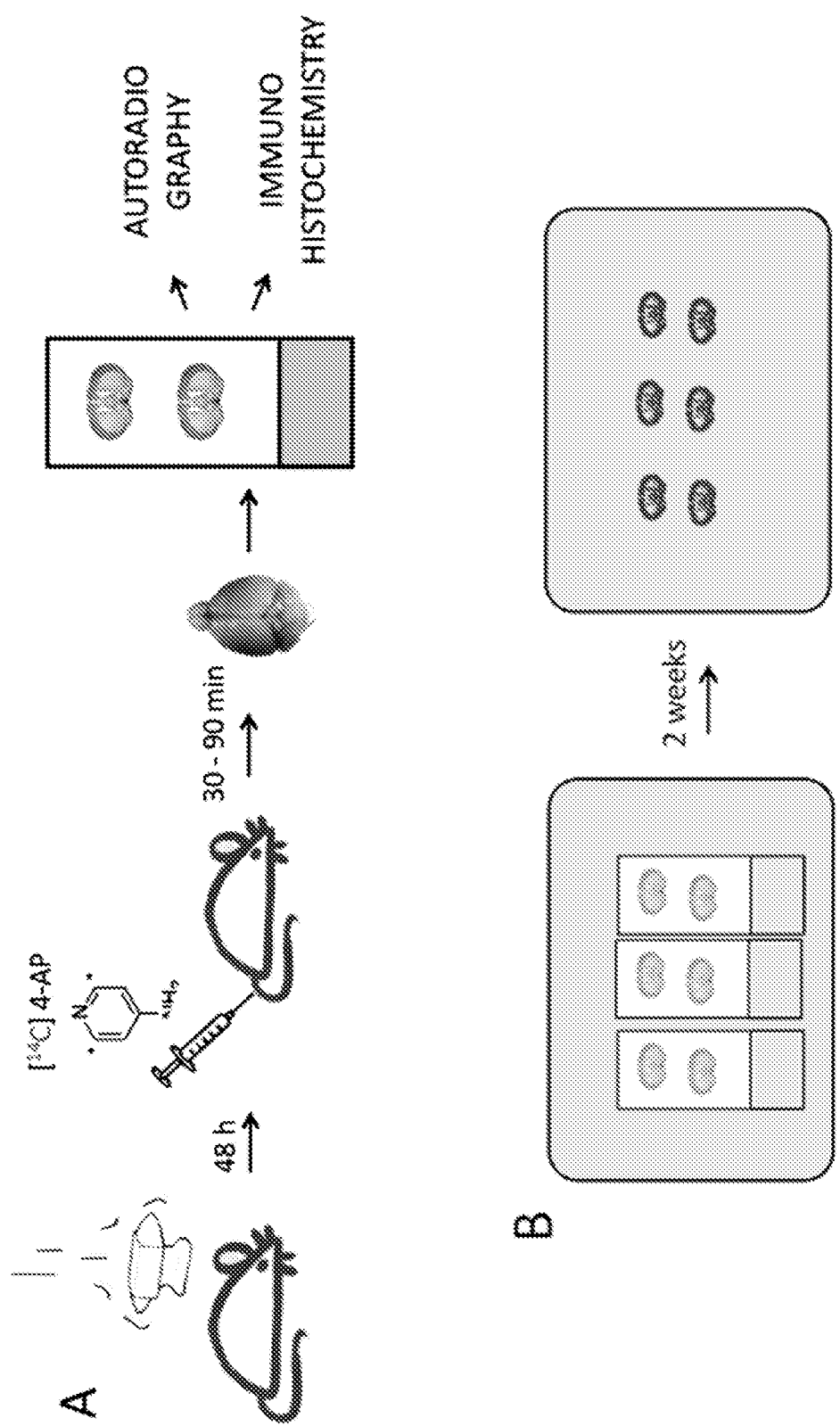

Example 16. (Prophetic) 4-AP Preferentially Localizes to TBI Lesions Using Autoradiography 4-AP has a higher uptake in demyelinated (injured) white matter areas than in the rest of the white matter. In order to determine if 4-AP localizes to areas of the brain affected by a traumatic brain injury, the inventors will conduct a similar experiment in a rat model of TBI (FIG. 9A). The inventors will induce traumatic brain injuries in rats using the controlled impact model. Afterwards, the animals will be injected with $^{14}$C-labeled 4-AP (0.1-0.5 μCi/g). The animals will be euthanized 30 to 90 min later and their brains removed. Thin sections of their brains will be prepared and the localization of the drug determined using autoradiography (FIG. 9B). Subsequently the lesioned areas will be examined by immunohistochemistry to identify the traumatic injured areas. The autoradiographic signal corresponding to those regions will be quantified and the results evaluated using analysis of variance (ANOVA).

We also plan to perform a similar experiment using [$^{14}$C] 2-deoxy-d-glucose (2-DG). 2-DG has a similar distribution pattern in the brain (higher uptake in grey matter areas than white matter areas). However, 2-DG it is not expected to accumulate in injured areas of the brain to a significant degree. This experiment will serve as a control and provide a preview of the comparison of [$^{18}$F]-labeled 4-AP with [$^{18}$F] FDG using PET.

Example 17 (Prophetic)—Compare the Distribution of 3-F-4-AP and 3-MEF-4-AP in the Brain of Animals with Demyelinating Lesions Using the same autoradiographic technique we will evaluate the brain distribution [$^{14}$C] 3-F-4-AP and [$^{14}$C] 3-MeF-4-AP. These will be the molecules used for PET imaging. Both of these molecules have similar affinity to K+ channels as 4-AP and better brain permeability. This experiment will allow us to identify the best candidate for imaging. In addition, we will include [$^{14}$C] 2-F-4-AP which has the same molecular weight as [$^{14}$C] 3-F-4-AP and very similar brain permeability but does not bind to K$^{+}$ channels to control for non-specific localization of this type of molecules.

Similar as with 4-AP, we will perform a dose-response and preblocking experiments in control rats to determine the best conditions for imaging. Once we optimize the conditions we will perform the experiments in lysolecithin-injected rats. Based on our statistical calculation, we estimate that in this experiment we will need around 6 rats per group. Similar as before, the results will be analyzed using ANOVA.

Example 18 (Prophetic)—Synthetic Methodology for [$^{18}$F] 3-F-4-AP and [$^{18}$F] 3-MEF-4-AP Fluorine-18 is the most appropriate radionuclide for PET as its low positron energy allows for sharper resolution, and its longer half-life (109.8 min vs. 20 min for $^{11}$C) allows for off-site production and commercialization. In order to be able to use fluorinated 4-APs as PET tracers, a quick radiolabeling strategy will be necessary ($^{18}$F half-life: 109 min). See FIG. 8.

The proposed synthesis of [$^{18}$F] 3-F-4-AP makes use of the recently developed method of using iodonium salts for high efficiency synthesis of aryl fluorides (Chun, et al., 2012). In comparison, [$^{18}$F] 3-MeF-4-AP possesses an aliphatic fluoride that it is expected to be facile to synthesize.

Example 19 (Prophetic)—Pet Imaging in Small Animal Models of TBI

Immediately after synthesizing the $^{18}$F-labeled compounds, a dynamic emission scan will be performed in 3D acquisition mode in the TBI induced animals using a GMI microPET/SPECT/CT system. The resolution of the microPET scanner is limited to ~1 mm. In addition, a post-mortem autoradiography will be conducted after the scan to further verify the localization of the tracer.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Acorda Therapeutics, Inc., Appln. No. 022250, Drug Approval Package, 2010 (http://www.accessdata.fda.gov/drugsatfda_docs/nda)
Advanced Organic Chemistry, Part B: Reactions and Synthesis, 4th Ed.; Carey and Sundberg (Eds.), Kluwer Academic/Plenum Publishers, NY, 2001.
Advanced Organic Chemistry, Reactions, Mechanisms, and Structure, 2nd Ed., March, McGraw Hill, 1977.
Ametamey et al., *Chem. Rev.*, 108:1501-1516, 2008.
Ampyra.com: http://goo.gl/fqcZo
Armstrong and Loboda, *Biophys. J.*, 81:895-904, 2001.
Arroyo et al., *J. Comp. Neurol.*, 479:424-434, 2004.
Arzneimittelforschung, 39(7):762-765, 1989.
Behi et al., *Immunology Lett.*, 96:11-26, 2005.
Berger, et al., *Arzneimittelforschung.* 39:762, 1989.
Blight, A. R. *Brain Res Bull* 1989, 22, 47-52.
Cai, et al., *Euro J Org Chem.* 2853, 2008.
Calabresi, In: *Multiple sclerosis and demyelinating conditions of the central nervous system,* Goldman and (Eds.), Cecil Medicine, 23rd Ed., PA, Saunders Elsevier, 2007.
Chun, et al., *Chem Commun (Camb)*. 48:9921, 2012.
Chun, et al., *J Org Chem.* 77(4):1931-8, 2012.
Coman et al., *Brain,* 129:3186-3195, 2006.
Compendium of Organic Synthetic Methods, Vol 1, 1971; Vol. 2, 1974; Vol. 3, 1977; Vol. 4, 1980; Vol. 5, 1984; and Vol. 6, 1985.
Comprehensive Organic Synthesis. Selectivity, Strategy & Efficiency in Modern Organic Chemistry, In 9 Volumes, Barry M. Trost, Editor-in-Chief, Pergamon Press, NY, 1993
Comprehensive Organic Transformations, 2nd Ed., Larock (Ed.), John Wiley & Sons, NY, 1999.
Devaux, et al., *J Neurophysio.* 87:1376, 2002.
Dolle, et al., *Curr Pharma Des.* 11:3221, 2005.
Fehlings, M. G. and Nashmi, R., *Brain Res* 1996, 736, 135-45.
Fox et al., Neurol Res, 35: 223-32, 2013.
Flygt, J et al., *Eur J Neurosci* 2013, 38, 2153-65.
Gao et al., *Neurochem. Res.,* 24:1181-1188, 1999.
Gonda, *Crit. Rev. Ther. Drug Carrier Sys.,* 6:273-313, 1990.
Goodman et al., *Lancet.,* 373:732-738, 2009.
Gruner, J. A. and Yee, A. K., *Brain Res* 1999, 816, 446-56.
Gutman, et al., *Pharmacol Rev.* 57:473, 2005.
*Handbook of Pharmaceutical Salts: Properties, and Use,* 2002.
Hayes, K. C, et al., *Paraplegia* 1993, 31, 216-24.
Hulkower et al., AJNR Am J Neuroradiol, 2013.
Kirsch and Narahashi, *Biophys. J.,* 22:507-512, 1978.
Konrad et al, Psychol Med 41: 1197-211, 2011.
Lee and Chi, *J. Org. Chem.,* 64:8567-8581, 1999.
Lee and Chi, *J. Organic Chem.,* 64:8576-8581, 1999.
Lee et al., *Bull. Korean Chem. Soc.,* 25(8):1225-1230, 2004.
Lee et al., *Science,* 334:639, 2011.
Lee et al., *Science,* 334:639-642, 2011.
Lee, et al., *J Org Chem.* 64:8576, 1999.
Leung et al., *Exp. Neurol.,* 227:232-235, 2011.
Lin et al., *J. Neurosci.,* 24:10074-10083, 2004.
Lundh et al., *J. Neurol. Neurosurg. Psychiatry,* 40(11):1109-1112, 1977.
Maddison and Newsom-Davis, *Cochrane Database Syst. Rev.,* CD003279, 2003.
March's Advanced Organic Chemistry, 3rd Ed., John Wiley & Sons, NY, 1985
March's Advanced Organic Chemistry: Reactions, Mechanisms, and Structure, 2007.
Martin and McFarland, *Crit. Rev. Clin. Lab. Sci.,* 32:121-182, 1995.
Matsushima and Morell, *Brain Pathol.,* 11:107-116, 2001.
McCormack, et al., *Neuron.* 12:301, 1994.
Mobinikhaledi and Foroughifar, *Phosphorus, Sulfur and Silicon,* 181:405-412, 2006.
Mochizuki, et al., *Bioorg Med Chem.* 19:1623, 2011.
Molecular Imaging and Contrast Agent Database (MICAD). National Center for Biotechnology Information (US). Bookshelf ID: NBK5330PMID: 20641179. http://www.ncbi.nlm.nih.gov/books/NBK5330/Morey,
R. A.; et al., *Hum Brain Mapp* 2012.
Murray and Newsom-Davis, *Neurology,* 31:265-271, 1981.
Oquendo et al., J Nerv Ment Dis 192: 430-4, 2004.
Olek, In: *Diagnosis of multiple sclerosis in adults,* Gonzalez-Scarano (Ed.), UpToDate, Walthan, Mass., 2011.
Organic Polymer Chemistry, 2nd Ed., Saunders et al. (Eds.), NY, 1973.
Oriuchi et al., *Cancer Sci.,* 97:1291-1297, 2006.
Owen et al., *Mult. Scler.,* 17:262-272, 2011.
Patton and Platz, *Adv. Drug Del. Rev.,* 8:179-196, 1992.
Pharmaceutical dosage form tablets, 1989
Pharmaceutical dosage forms and drug delivery systems, 1995
Polymer Science, Gowariker et al. (Eds.), John Wiley & Sons, NY, 1986. These are incorporated herein by reference.
*Prog. Clin. Biol. Res.,* 146:1-554. 1984.
Protecting Groups in Organic Synthesis, 2nd Ed., Greene and Wutz, John Wiley & Sons, NY, 1991.
Rasband et al., *J. Neurosci.,* 18:36-47, 1998.
Remington—The science and practice of pharmacy, 2000
Ritchie et al., *Nature,* 294:257-259, 1981.
Schwarzbold et al., Neuropsychiatr Dis Treat, 4: 797-816, 2008.
Sharp, D. J. and Ham, T. E. *Curr Opin Neurol* 2011, 24, 558-63.
Sherratt et al., *Nature,* 283:570-572, 1980.
Sherratt, et al., *Nature.* 283:570, 1980.
Smith et al., *Eur. J. Medicinal Chem.,* 40:908-917, 2005.
Soni and Kam, *Anaesth Intensive Care,* 10(2):120-126, 1982.
Spivey et al., *J. Org. Chem.,* 64(26):9437, 1999.
Spivey, et al., *J Org Chem.* 64:9430, 1999.
Stankoff et al., *Ann. Neurol.,* 69:673-680, 2011.
Starace and Bezanilla, *Nature,* 427:548-552, 2004.
Stefani and Bezanilla, *Methods Enzymol.,* 293:300-318, 1998.
Stidworthy et al., *Brain,* 127:1928-1941, 2004.
Stys et al., *Brain Res.,* 546(1):18-32, 1991.
Stys, et al., *Brain Res.* 546:18, 1991.
Sugano, et al., *J Biomolec Screening.* 6:189, 2001.
Sun et al., *J. Neurophysiol.,* 103:469-478, 2010.
Sun, *J. Chem. Inf. Comput. Sci.,* 44(2):748-757, 2004.

Textbook of Polymer Chemistry, 3$^{rd}$ Ed., Billmeyer (Ed.), John Wiley & Sons, NY, 1984.
Traka et al., *Brain*, 133:3017-3029, 2010.
van Reekum et al., J Neuropsychiatry Clin Neurosci, 12: 316-27, 2000.
Vasterling et al., Br J Psychiatry, 201: 186-92, 2012.
Wang et al., *Neuron.*, 15:1337-1347, 1995.
Waxman and Ritchie, *Ann. Neurol.*, 33:121-136, 1993.
Whelan-Goodinson et al., J Head Trauma Rehabil 24: 324-32, 2009.
Wulff et al., *Nat. Rev. Drug Discov.*, 8:982-1001, 2009.
Yeh et al., *Biophys J.*, 16(1):77-81, 1976.
Zamvil and Steinman, *Annu. Rev. Immunol.*, 8579-8621, 1990.
Zhou et al., *J. Med. Chem.*, 52:2443-2453, 2009.
Zhou, et al., *J Med Chem.* 52:2443, 2009.

The invention claimed is:

1. An imaging method comprising administering to a subject [$^{18}$F]3-fluoro-4-aminopyridine and detecting the [$^{18}$F]3-fluoro-4-aminopyridine in the subject.

2. A method for diagnosing a demyelinating disease or evaluating the progression of a demyelinating disease comprising administering to a subject [$^{18}$F]3-fluoro-4-aminopyridine and detecting the [$^{18}$F]3-fluoro-4-aminopyridine in the subject by a radiodiagnostic method.

3. The method of claim 2, wherein the demyelinating disease is multiple sclerosis, spinal cord compression, ischemia, acute disseminated encephalomyelitis, optic neuromyelitis, leukodystrophy, progressive multifocal leukoencephalopathy, metabolic disorders, toxic exposure, congenital demyelinating disease, peripheral neuropathy, encephalomyelitis, central pontine myelolysis, Anti-MAG Disease, Guillain-Barre syndrome, chronic inflammatory demyelinating polyneuropathy, or multifocal motor neuropathy (MMN).

4. The method of claim 1, wherein a dose is from about 0.005 to 50 mCi.

5. The method of claim 2, wherein the radiodiagnostic method is Positron Emission Tomography (PET), PET-Time-Activity Curve (TAC), PET-Magnetic Resonance Imaging (MRI), or PET/CT.

6. The method of claim 5, wherein the radiodiagnostic method is PET.

7. The method of claim 2, further comprising quantifying an amount of the [$^{18}$F]3-fluoro-4-aminopyridine in the subject.

8. The method of claim 2, wherein a demyelinated region in an axon in the subject is detected by detecting the [$^{18}$F]3-fluoro-4-aminopyridine.

9. The method of claim 2, wherein the [$^{18}$F]3-fluoro-4-aminopyridine blocks potassium channels located at a demyelinated region in an axon in the subject.

10. A method for diagnosing traumatic brain injury or evaluating the progression of traumatic brain injury in a subject comprising administering to the subject [$^{18}$F]3-fluoro-4-aminopyridine and detecting the [$^{18}$F]3-fluoro-4-aminopyridine in the subject.

11. The method of claim 10, wherein the subject is at risk for traumatic brain injury or a concussion.

12. The method of claim 10, wherein the detecting is affected by a radiodiagnostic method.

13. The method of claim 12, wherein the radiodiagnostic method is Positron Emission Tomography (PET), PET-Time-Activity Curve (TAC), PET-Magnetic Resonance Imaging (MRI), or PET/CT.

14. The method of claim 13, wherein the radiodiagnostic method is PET.

15. The method of claim 10, further comprising quantifying the amount of the [$^{18}$F]3-fluoro-4-aminopyridine in the subject.

16. The method of claim 10, wherein a demyelinated region in an axon in the subject is detected by detecting the [$^{18}$F]3-fluoro-4-aminopyridine and an increase in demyelination indicates traumatic brain injury.

17. The method of claim 10, wherein the [$^{18}$F]3-fluoro-4-aminopyridine blocks potassium channels located at a demyelinated region in an axon in the subject.

* * * * *